United States Patent
Allen, IV et al.

(10) Patent No.: US 9,539,049 B2
(45) Date of Patent: *Jan. 10, 2017

(54) MONOPOLAR PENCIL WITH INTEGRATED BIPOLAR/LIGASURE TWEEZERS

(71) Applicant: COVIDIEN LP, Mansfield, MA (US)

(72) Inventors: James D. Allen, IV, Broomfield, CO (US); Stephen M. Kendrick, Broomfield, CO (US); Dennis W. Butcher, Longmont, CO (US); Daniel A. Joseph, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,992

(22) Filed: Apr. 22, 2015

(65) Prior Publication Data

US 2015/0223862 A1    Aug. 13, 2015

Related U.S. Application Data

(63) Continuation of application No. 13/344,729, filed on Jan. 6, 2012, now Pat. No. 9,023,035.

(51) Int. Cl.
*A61B 18/12* (2006.01)
*A61B 18/14* (2006.01)
*A61B 18/00* (2006.01)

(52) U.S. Cl.
CPC ........... *A61B 18/12* (2013.01); *A61B 18/1442* (2013.01); *A61B 2018/00702* (2013.01);
(Continued)

(58) Field of Classification Search
CPC .................................................. A61B 18/1442
See application file for complete search history.

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| CN | 201299462 | 9/2009 |
| DE | 2415263 A1 | 10/1975 |

(Continued)

OTHER PUBLICATIONS

Int'l Search Report EP 05020532 dated Jan. 10, 2006.
(Continued)

*Primary Examiner* — Carl H Layno
*Assistant Examiner* — Jennifer Ghand

(57) ABSTRACT

An electrosurgical pencil with integrated tweezers includes an elongated housing having an open distal end and an actuator operatively associated therewith. First and second jaw members extend distally through the open distal end of the elongated housing and are transitionable between a closed position and an open position upon actuation of an actuator. One or both of the jaw members is configured to treat tissue with monopolar energy and both jaw members are configured to treat tissue with bipolar energy. One or more switches is operably coupled to a controller disposed in the housing and configured to activate the first and second jaw members to treat tissue with monopolar and bipolar energy.

6 Claims, 24 Drawing Sheets

(52) U.S. Cl.
CPC .............. *A61B 2018/00773* (2013.01); *A61B 2018/00922* (2013.01); *A61B 2018/00928* (2013.01); *A61B 2018/00958* (2013.01); *A61B 2018/00994* (2013.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,472,442 A | 12/1995 | Klicek |
| 5,527,313 A * | 6/1996 | Scott et al. ................ 606/51 |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,214,003 B1 | 4/2001 | Morgan et al. |
| D449,886 S | 10/2001 | Tetzlaff et al. |
| D453,923 S | 2/2002 | Olson |
| D454,951 S | 3/2002 | Bon |
| 6,355,034 B2 | 3/2002 | Cosmescu |
| D457,958 S | 5/2002 | Dycus et al. |
| D457,959 S | 5/2002 | Tetzlaff et al. |
| H2037 H | 7/2002 | Yates et al. |
| 6,461,352 B2 | 10/2002 | Morgan et al. |
| D465,281 S | 11/2002 | Lang |
| D466,209 S | 11/2002 | Bon |
| 6,702,812 B2 | 3/2004 | Cosmescu |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,112,199 B2 | 9/2006 | Cosmescu |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,503,917 B2 | 3/2009 | Sartor et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 9,023,035 B2 * | 5/2015 | Allen et al. ................ 606/41 |
| 2005/0113825 A1 | 5/2005 | Cosmescu |
| 2005/0113827 A1 | 5/2005 | Dumbauld et al. |
| 2005/0137590 A1 * | 6/2005 | Lawes et al. ................ 606/45 |
| 2006/0041257 A1 | 2/2006 | Sartor et al. |
| 2007/0078458 A1 | 4/2007 | Dumbauld et al. |
| 2007/0106297 A1 * | 5/2007 | Dumbauld ........ A61B 18/1445 606/51 |
| 2008/0319442 A1 | 12/2008 | Unger et al. |
| 2009/0248008 A1 | 10/2009 | Kerr |
| 2009/0261804 A1 | 10/2009 | McKenna et al. |
| 2010/0087814 A1 | 4/2010 | Desinger et al. |
| 2011/0112530 A1 * | 5/2011 | Keller .................... A61B 18/14 606/42 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 20 2007 009317 U1 | 8/2007 |
| DE | 202007009165 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 20013400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |

(56) References Cited

FOREIGN PATENT DOCUMENTS

| WO | 0115614 A1 | 3/2001 |
|---|---|---|
| WO | 0154604 A1 | 8/2001 |
| WO | 2005/110264 A2 | 11/2005 |

OTHER PUBLICATIONS

Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

(56) References Cited

OTHER PUBLICATIONS

Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/ Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.

(56) References Cited

OTHER PUBLICATIONS

McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011 John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.

* cited by examiner

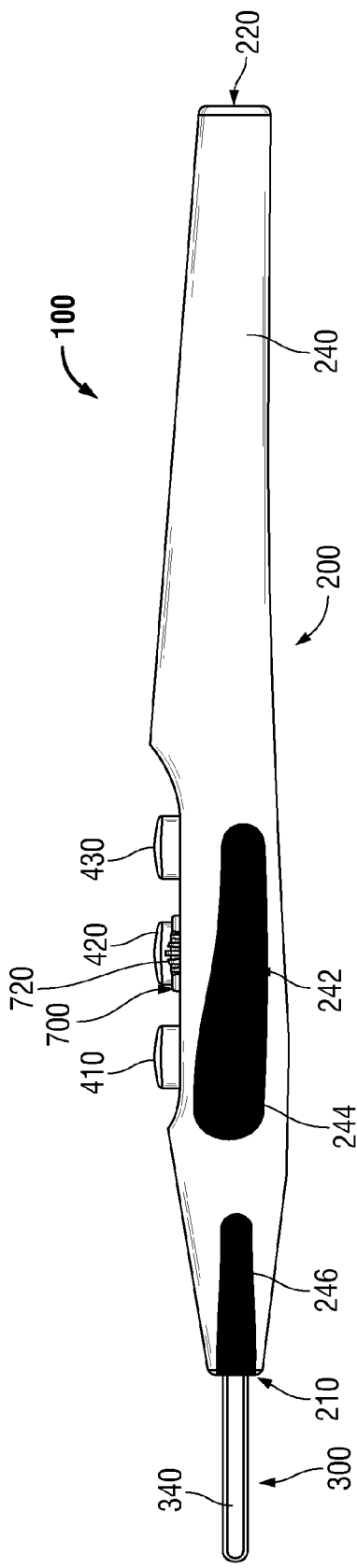
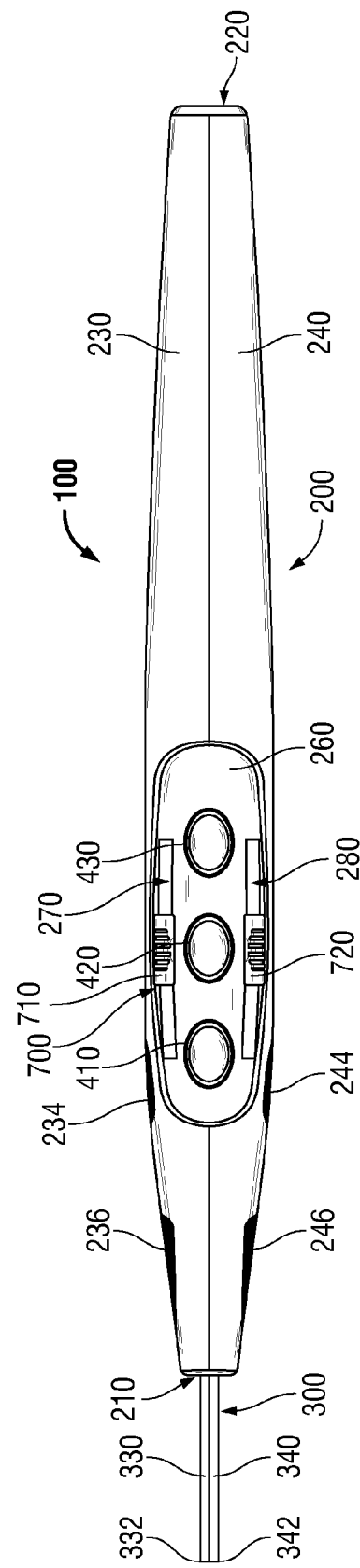

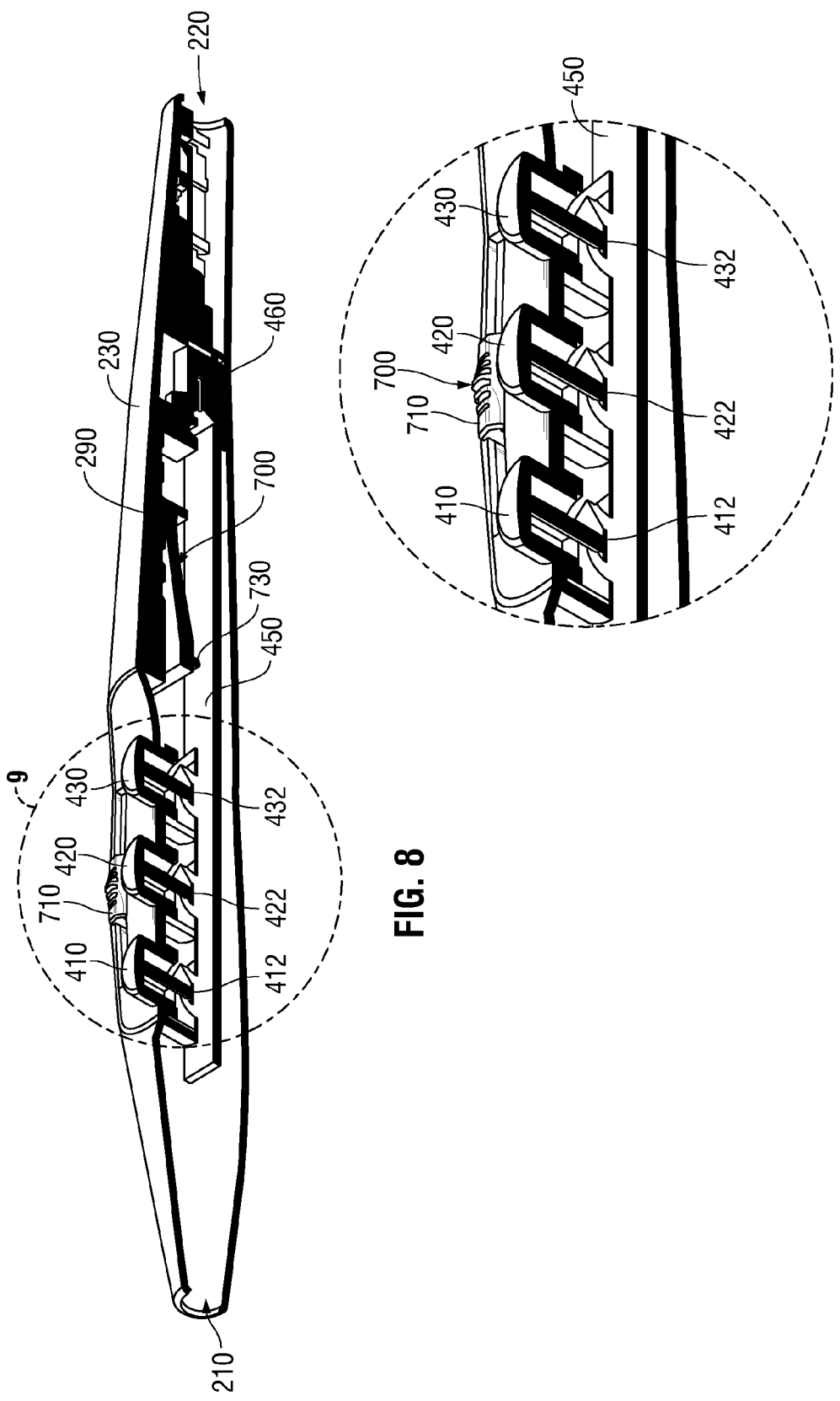

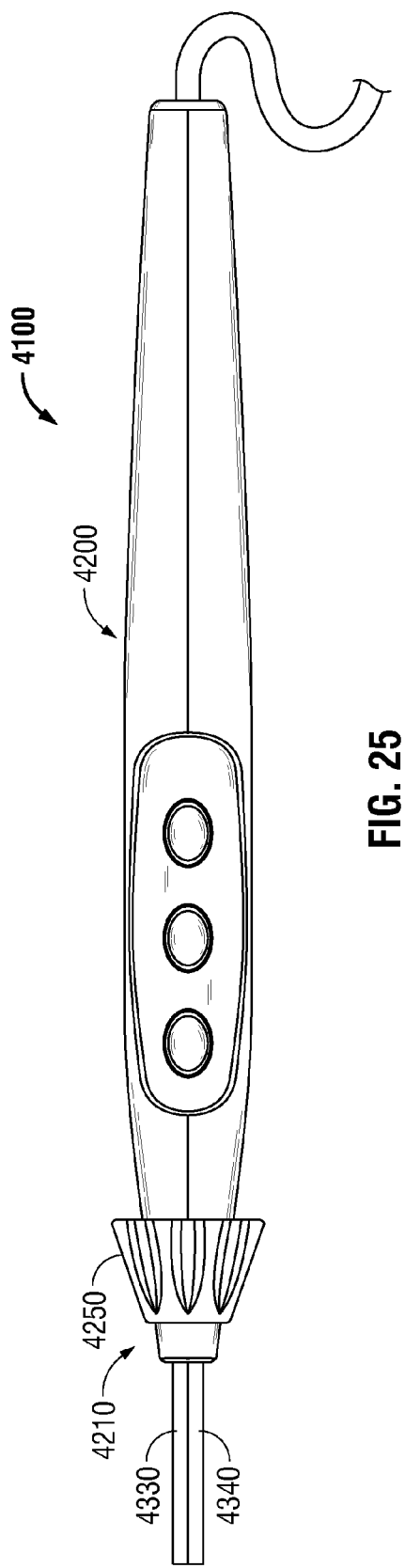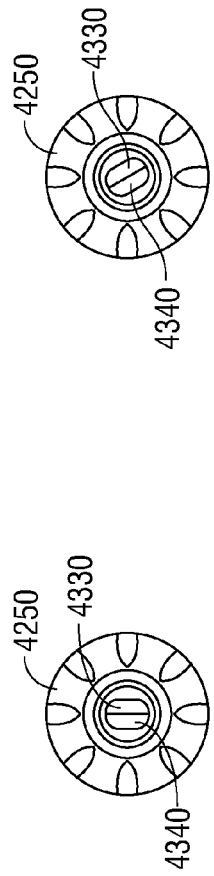
FIG. 25
FIG. 26
FIG. 27

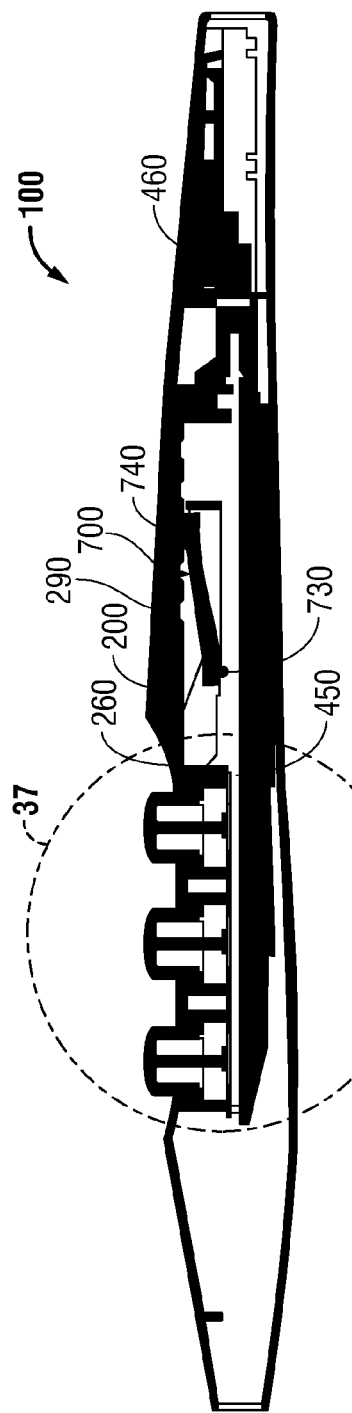
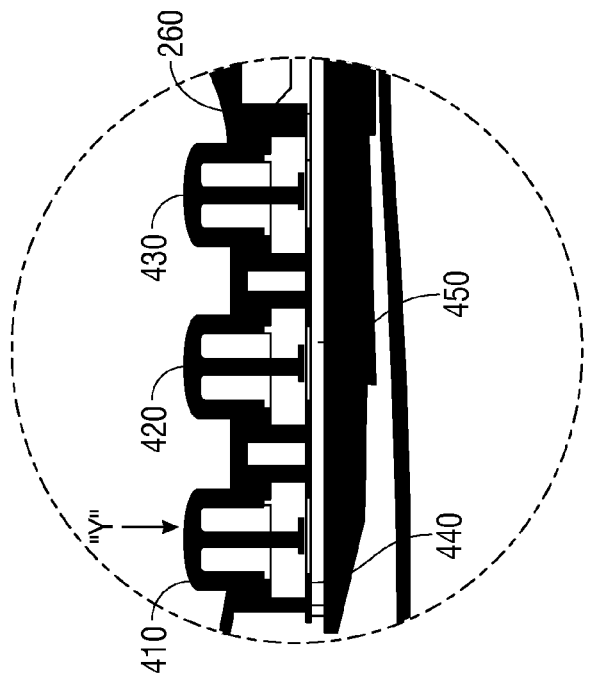
FIG. 36
FIG. 37

MONOPOLAR PENCIL WITH INTEGRATED BIPOLAR/LIGASURE TWEEZERS

CROSS-REFERENCE TO RELATED APPLICATIONS

This application is a continuation application of U.S. patent application Ser. No. 13/344,729, filed on Jan. 6, 2012, now U.S. Pat. No. 9,023,035, the entire contents of which are incorporated herein by reference.

BACKGROUND

1. Technical Field

The present disclosure relates generally to electrosurgical instruments and, more particularly, to an electrosurgical pencil configured for both monopolar and bipolar use.

2. Background of Related Art

Electrosurgical instruments have become widely used by surgeons in recent years. By and large, most electrosurgical instruments are hand-held instruments, e.g., an electrosurgical pencil or electrosurgical forceps, which transfer radio-frequency (RF) electrical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of electric spark to biological tissue, for example, human flesh or the tissue of internal organs, without significant cutting. The spark is produced by bursts of radio-frequency electrical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass. Electrosurgical forceps utilize both mechanical clamping action and electrical energy to effect hemostasis by heating the tissue and blood vessels to coagulate, cauterize, seal, cut, desiccate, and/or fulgurate tissue.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode (usually a plate positioned on the patient's thigh or back) as the means to complete the electrical circuit between the electrosurgical generator and the patient. In bipolar electrosurgery, the electrosurgical device includes two electrodes that are located in proximity to one another for the application of current between their surfaces. Bipolar electrosurgical current travels from one electrode, through the intervening tissue to the other electrode to complete the electrical circuit.

As used herein the term "electrosurgical pencil" is intended to include instruments which have a handpiece that is attached to an active electrode and which is used to cauterize, coagulate and/or cut tissue. Typically, the electrosurgical pencil may be operated by a handswitch or a foot switch. The active electrode is an electrically conducting element that is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue and a blend wave form is somewhere between a cut and coagulate wave from.

SUMMARY

The present disclosure is directed to an electrosurgical pencil with integrated ligasure tweezers. In accordance with one aspect of the present disclosure the electrosurgical pencil includes an elongated housing having an open distal end and including an actuator operatively associated therewith. First and second jaw members extend distally through the open distal end of the elongated housing and are transitionable between a closed position and an open position upon actuation of an actuator. One or both of the jaw members are configured to treat tissue with monopolar energy and both jaw members are configured to treat tissue with bipolar energy. One or more switches are operably coupled to a controller disposed in the housing and configured to activate the first and second jaw members to treat tissue with monopolar and bipolar energy.

It is contemplated that the electrosurgical pencil may further include a sensor operably coupled to the pencil and configured to sense tissue disposed between the jaw members. The sensor provides a signal to the controller to disable monopolar activation if tissue is sensed between the jaw members and to disable bipolar activation if no tissue is sensed between the jaw members.

It is also contemplated that the electrosurgical pencil may further include an intensity controller that controls the amount of energy delivered to tissue when treating tissue with monopolar energy. The intensity controller would preferably be in the form of a slide potentiometer or could include a pressure sensitive activator that adjusts the amount of electrosurgical energy supplied based on the amount of pressure applied to the intensity controller.

The jaw members may be biased in the second, closed position and may be electrically isolated from one another such that the jaw members may treat tissue with bipolar energy when the jaw members are disposed in the second, closed position.

The actuator may protrudes from a side portion of the elongated housing and the side portion of the elongated housing. The elongated housing may include two flexible portions disposed on opposite sides thereof. The flexible portions are adjacent to the actuator such that compression of the two flexible portions in a direction substantially perpendicular to the longitudinal axis results in actuation of the actuator.

The open distal end of the elongated housing may include a flexible section. The flexible section is configured to allow the first and second jaw members to be radially spaced at a diameter larger than the open distal end of the elongated housing when in the open position.

According to another aspect of the present disclosure, an electrosurgical pencil is provided which includes an elongated housing having first and second jaw members extending through a distal end thereof. The first and second jaw members are transitionable between a first position wherein the jaw members are disposed in spaced relation relative to one another and a second position wherein the jaw members are approximated relative to one another. One or both of the jaw members are configured to treat tissue with monopolar energy and both jaw members are configured to treat tissue with bipolar energy. An actuator is operably coupled to the jaw members and actuatable to transition the jaw members between the first and second positions. The actuator is operably coupled to a controller that senses the disposition of the jaw members. A switch is disposed in the housing in operative communication with the controller and is configured to activate the jaw members with bipolar energy if the jaw members are disposed in the first position and to activate at least one of jaw members with monopolar energy if the jaw members are disposed in the second position.

It is contemplated that the surgical pencil may include an intensity controller that controls the amount of energy delivered to tissue when treating tissue with monopolar energy. It is also contemplated that the intensity controller may be a slide potentiometer or may include a pressure sensitive activator that adjusts the amount of electrosurgical energy delivered to tissue based on the amount of pressure applied to the intensity controller.

It is also contemplated that the actuator may be pressure sensitive such that the actuator adjusts the position of the jaw members relative to one another based on the amount of pressure applied to the actuator.

It is further contemplated that the jaw members may be biased in the second, closed position and that the actuator may protrude from a side portion of the elongated housing. The side portion of the elongated housing may include a flexible portion covering the actuator where the application of force to the flexible portion in a direction substantially perpendicular to the longitudinal axis results in actuation of the actuator.

According to another aspect of the present disclosure, an electrosurgical pencil is provided which includes an elongate housing having first and second jaw members extending through a distal end thereof. The first and second jaw members are transitionable between a closed position in which the jaw members are configured to treat tissue with monopolar energy and an open position in which the jaw members are configured to treat tissue with bipolar energy. A controller is disposed within the elongated housing and configured to sense whether the first and second jaw members are in the open or closed position and to automatically configure the jaw members to treat tissue with monopolar energy when the jaw members are in the closed position and bipolar energy when the jaw members are in the open position.

These and other features will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIG. 3 is a side view of the electrosurgical pencil of FIG. 1;

FIG. 4 is a top view of the electrosurgical pencil of FIG. 1;

FIG. 8 is a side, cut-away view of the housing and electrical assembly of the electrosurgical pencil of FIG. 1;

FIG. 9 is an enlarged view of the indicated area of detail of FIG. 8;

FIG. 25 is a top view of an electrosurgical pencil in accordance with another embodiment of the present disclosure;

FIG. 26 is a front view of the electrosurgical pencil of FIG. 25 with the jaws in a first configuration;

FIG. 27 is a front view of the electrosurgical pencil of FIG. 25 with the jaws rotated to a second configuration;

FIG. 36 is a side, cut-away view of the electrosurgical pencil of FIG. 1 showing the electrical assembly;

FIG. 37 is an enlarged view of the indicated area of detail of FIG. 36;

DETAILED DESCRIPTION

Figure 1:
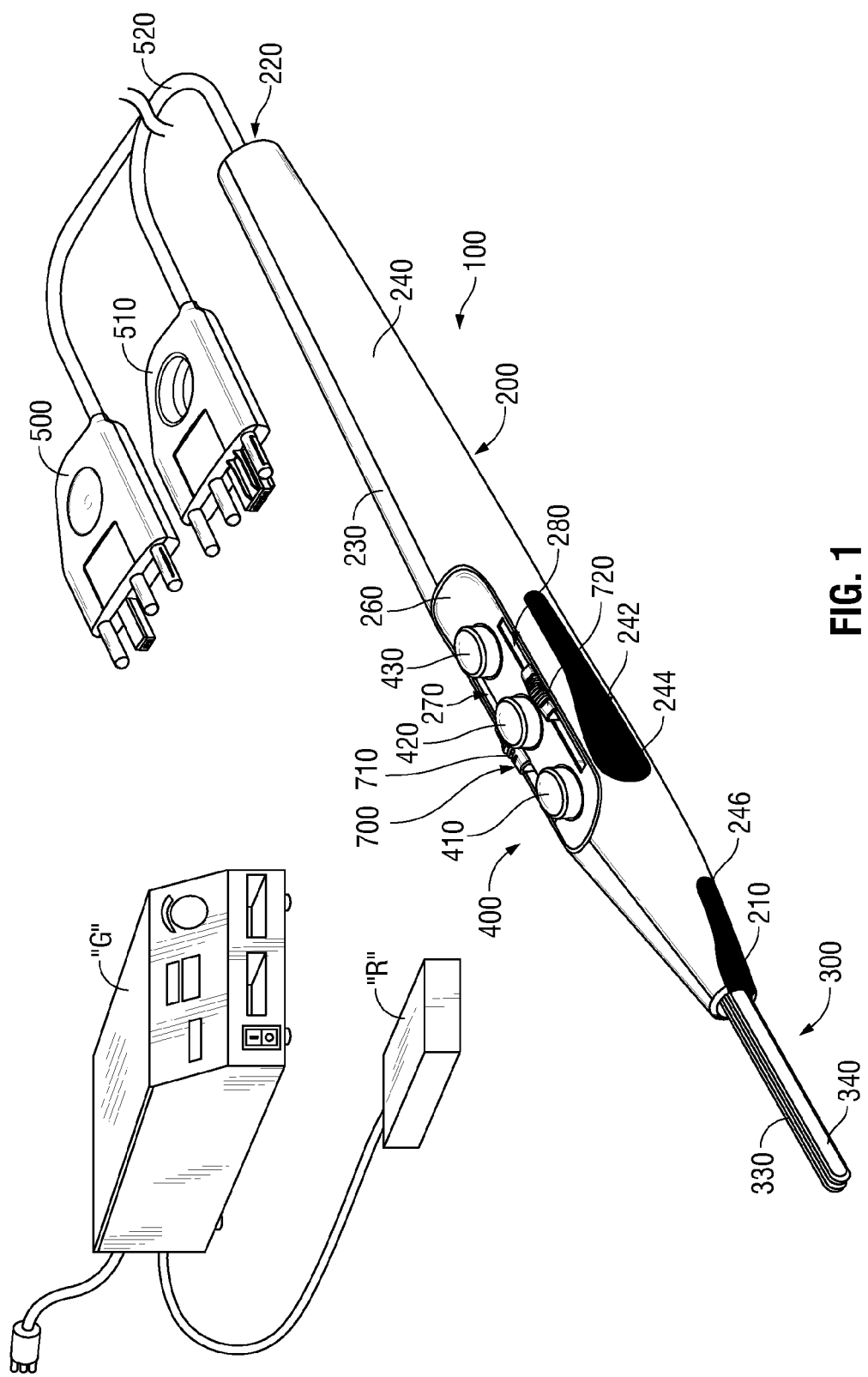
FIG. 1 is a perspective view of an electrosurgical system including an electrosurgical pencil in accordance with the present disclosure.

Particular embodiments of the presently disclosed electrosurgical pencil are described in detail with reference to the drawing figures wherein like reference numerals identify similar or identical elements. As used herein, the term "distal" refers to that portion which is further from the user while the term "proximal" refers to that portion which is closer to the user or surgeon.

FIG. 1 sets forth a perspective view of an electrosurgical system including an electrosurgical pencil 100 constructed in accordance with one embodiment of the present disclosure. Electrosurgical pencil 100 includes an elongated housing 200, a jaw assembly 300 and an electrical assembly 400. Housing 200 includes a distal opening 210, through which jaw assembly 300 extends, and a proximal opening 220, through which cable 520 extends. Housing 200 may be made of multiple sections such as, for example, side shell portions 230 and 240, or housing 200 may be made of a top half shell portion (not shown) and a bottom half shell portion (not shown). Shell portions 230, 240 may be bonded together using methods known by those skilled in the art, e.g., sonic energy, adhesives, snap-fit assemblies, etc.

As seen in FIG. 1, electrosurgical pencil 100 may be coupled to a conventional electrosurgical generator "G" via a plug 500. Plug 500 may be utilized for both monopolar electrosurgey and bipolar electrosurgery. Alternatively, a second plug 510 may also be included where each plug 500, 510 is used for independent modes of operation including bipolar or monopolar modes. Both plugs 500, 510 may be coupled to electrosurgical pencil 100 via the same cable 520. Alternatively, each plug 500, 510 may couple to electrosurgical pencil via separate cables (not shown). One such plug configuration is shown in commonly owned U.S. Pat. No. 7,503,917.

Figure 5:
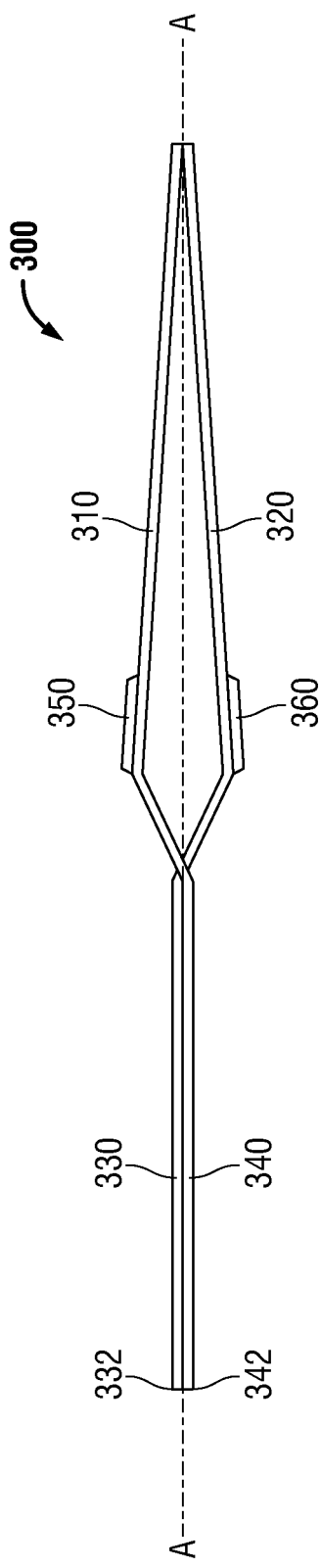
FIG. 5 is a top view of the jaw assembly of the electrosurgical pencil of FIG. 1 with jaw members in the second, closed position.
Figure 6:
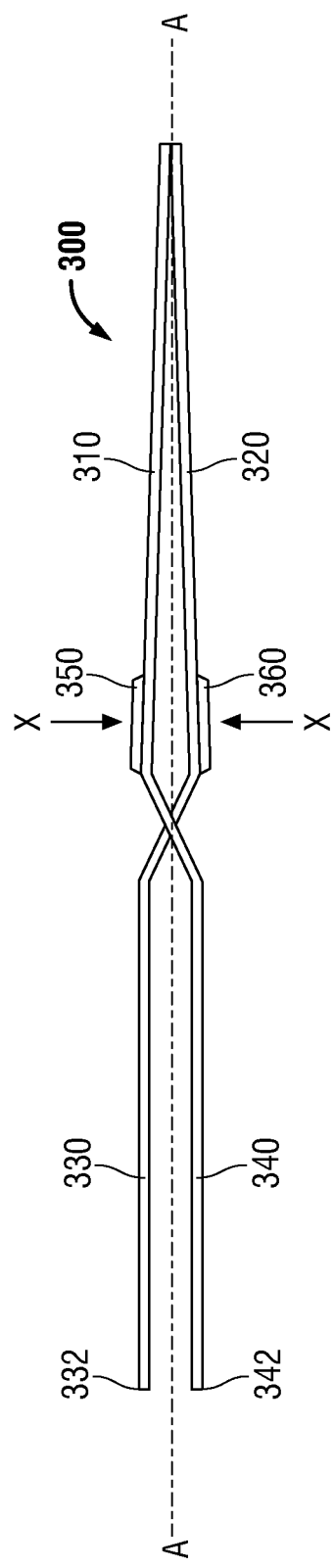
FIG. 6 is a top view of the jaw assembly of the electrosurgical pencil of FIG. 1 with jaw members in the first, open position.

Referring now to FIGS. 5 and 6, jaw assembly 300 defines a longitudinal axis A-A and includes body portions 310, 320, jaw members 330, 340 extending distally from body portions 310, 320, distal end portions 332, 342 disposed at the ends of jaw members 330, 340, respectively, and actuators 350, 360 disposed on body portions 310, 320. Jaw members 330, 340 are selectively transitionable relative to one another upon actuation of actuators 350, 360 in an inward direction "X", as shown in FIG. 6. Body portions 310, 320 are disposed within housing 200 and jaw members 330, 340 extend distally through distal end 220 of housing 200. Jaw members 330, 340 may be are fabricated from a conductive type material, such as, for example, stainless steel, or are coated with an electrically conductive material. Jaw members 330, 340 may also be electrically isolated from one another and may receive electrosurgical energy in both a monopolar and bipolar fashion, as explained in more detail below. Jaw members 330, 340 are electrically connected to a voltage divider network 450 (FIGS. 7 and 33) as explained in more detail below with regard to electrical assembly 400.

Figure 2:
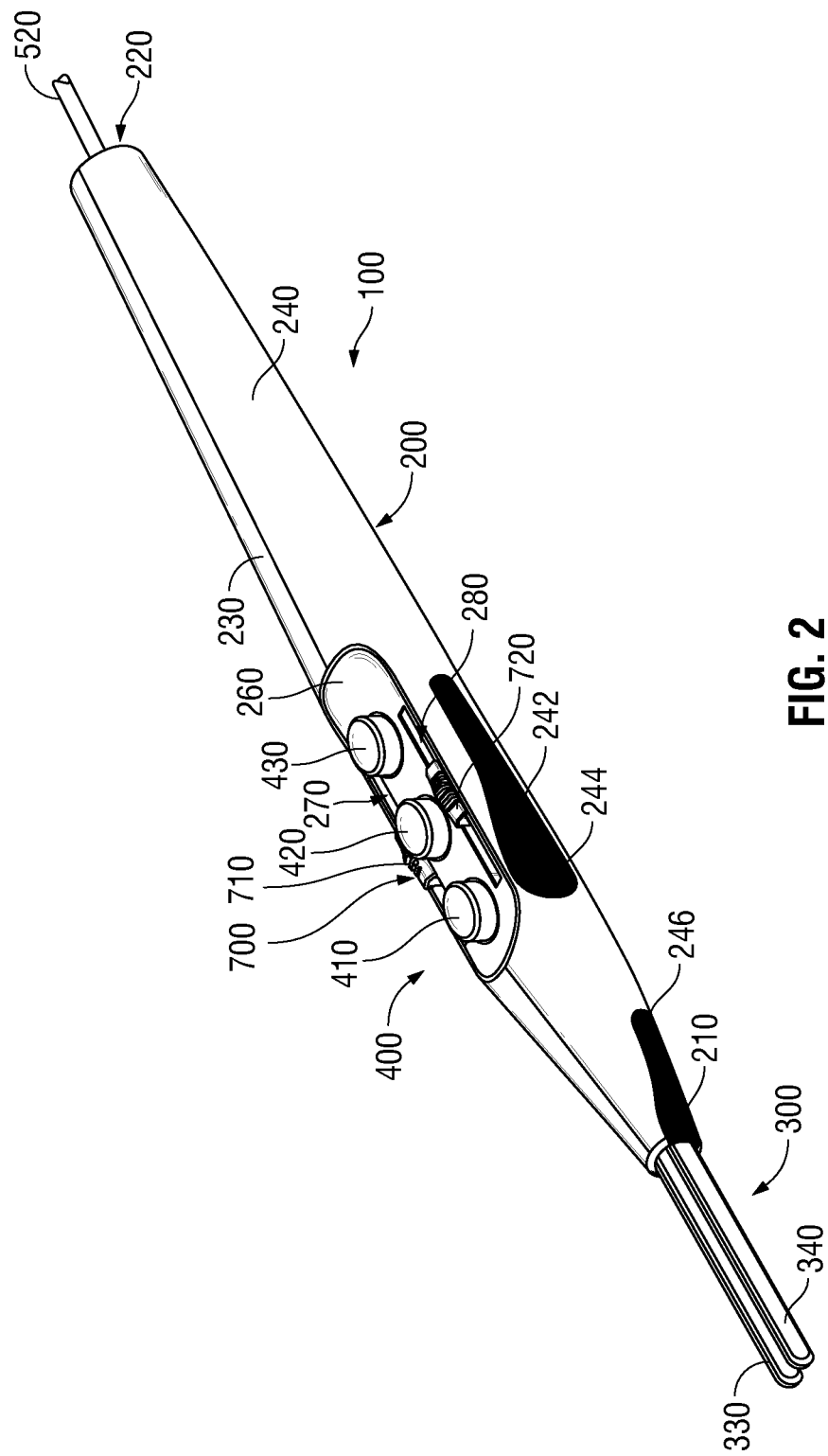
FIG. 2 is a perspective view of the electrosurgical pencil of FIG. 1 with jaw members in the first, open position.

Actuators 350, 360 extend through openings 232, 242 defined in shell portions 230 and 240 on opposite sides of housing 200. (See FIG. 7). Shell portions 230, 240 include flexible portions 234, 244 covering openings 232, 242 that allow a surgeon to actuate actuators 350, 360 in a hermetically sealed environment. Shell portions 230, 240 may also include flexible sections 236, 246 disposed at distal end 210 of housing 200 to provide jaw members 330, 340 with a greater range of motion. (See FIGS. 4 and 7). Actuators 350, 360 are actuatable to transition jaw members 330 and 340 between a first, open position where jaw members 330, 340 are spaced relative to one another (FIGS. 2 and 6) to receive tissue therebetween and a second, closed position where jaw members 330, 340 are approximated relative to one another (FIGS. 1 and 5). Jaw members 330, 340 are initially biased in the second, closed position as shown in FIGS. 1 and 5. Actuators 350, 360 allow for mechanical actuation of jaw members 330, 340 by moving body portions 310, 320 relative to one another. Alternatively, actuators 350, 360 may be in the form of a button or a switch (not shown) that allows for actuation of jaw members 330, 340 in a different manner as known in the art such as, for example, an electrical motor. The spacing of jaw members 330, 340 relative to one another (i.e., for receiving tissue) is adjusted based on the amount of pressure exerted on actuators 350, 360. For example, as the pressure being applied to actuators 350, 360 in the inward direction "X" is increased, the spacing between body portions 310, 320 is decreased and the spacing between jaw members 330, 340 is conversely increased. As explained below, each jaw member 330, 340 connects to an electrosurgical energy source "G" such that jaw members 330, 340 can treat tissue with electrosurgical energy. (See FIG. 1).

In use, a physician may utilize electrosurgical pencil 100 in either a monopolar mode or a bipolar mode as described below. When in a monopolar mode, the surgeon does not actuate actuators 350, 360 and jaw members 330, 340 are oriented in the second, closed position. Energy may then be applied via jaw members 330 and/or 340 to tissue in conjunction with a return pad "R". (See FIG. 1). Electrosurgical energy flows through one or both jaw members 330, 340, through the tissue, and into the return pad as further described below with relation to electrical assembly 400. When the bipolar mode is used, the surgeon exerts pressure on actuators 350, 360 in an inward direction "X" to increase the spacing between jaw members 330 and 340 and manipulates electrosurgical pencil 100 such that a portion of tissue is disposed between jaw members 330 and 340. The surgeon then releases actuators 350 and 360, thereby allowing the jaw members 330 and 340 to approximate relative to one another to close onto or clamp the portion of tissue disposed therebetween. The tissue is clamped due to the pressure exerted by the spring bias of the body portions 310 and 320. Particularly, the spring bias provides a pressure of about 3 $kg/cm^2$ to about 16 $kg/cm^2$ between jaw members 330 and 340.

When the desired tissue is clamped between jaw members 330 and 340, the surgeon may activate bipolar energy or alternatively bipolar energy may be automatically delivered to jaw members 330 and 340 as described below in relation to electrical assembly 400. In bipolar mode no return pad is included or necessary. Additionally, a safety switch "S3" (FIG. 35) may be included to preclude bipolar activation when the jaw members 330 and 340 are disposed in the second, closed position. A second safety switch "S3'" (FIG. 35) may also be included to preclude monopolar activation when the jaw members 330 and 340 are disposed in the first, open position. Safety switches "S3" and "S3'" may be mechanical, electrical or electro-mechanical.

The operational features of the electrical assembly 400 and intensity controller 700 are described below with reference to FIGS. 8, 9 and 32-39. Safety switches "S3" and "S3'" are also described in more detail below.

Figure 10:
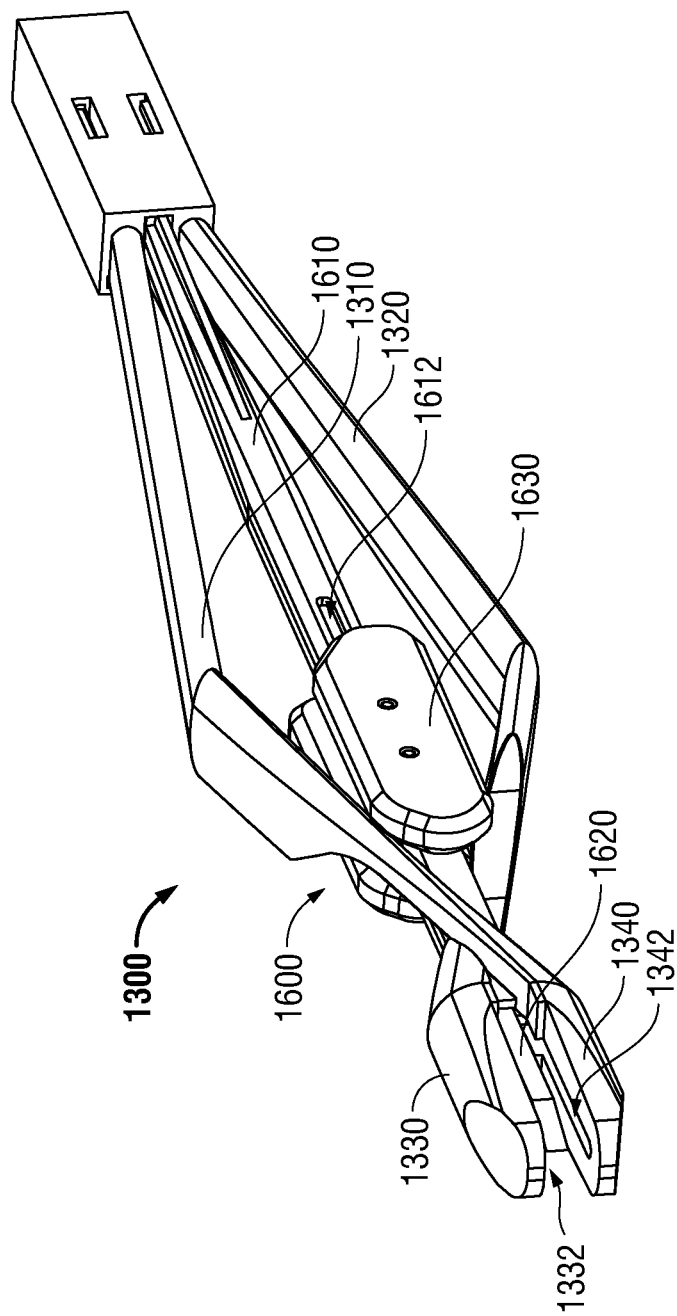
FIG. 10 is a perspective view of an alternate embodiment of the electrosurgical pencil in accordance with the present disclosure.
Figure 11:
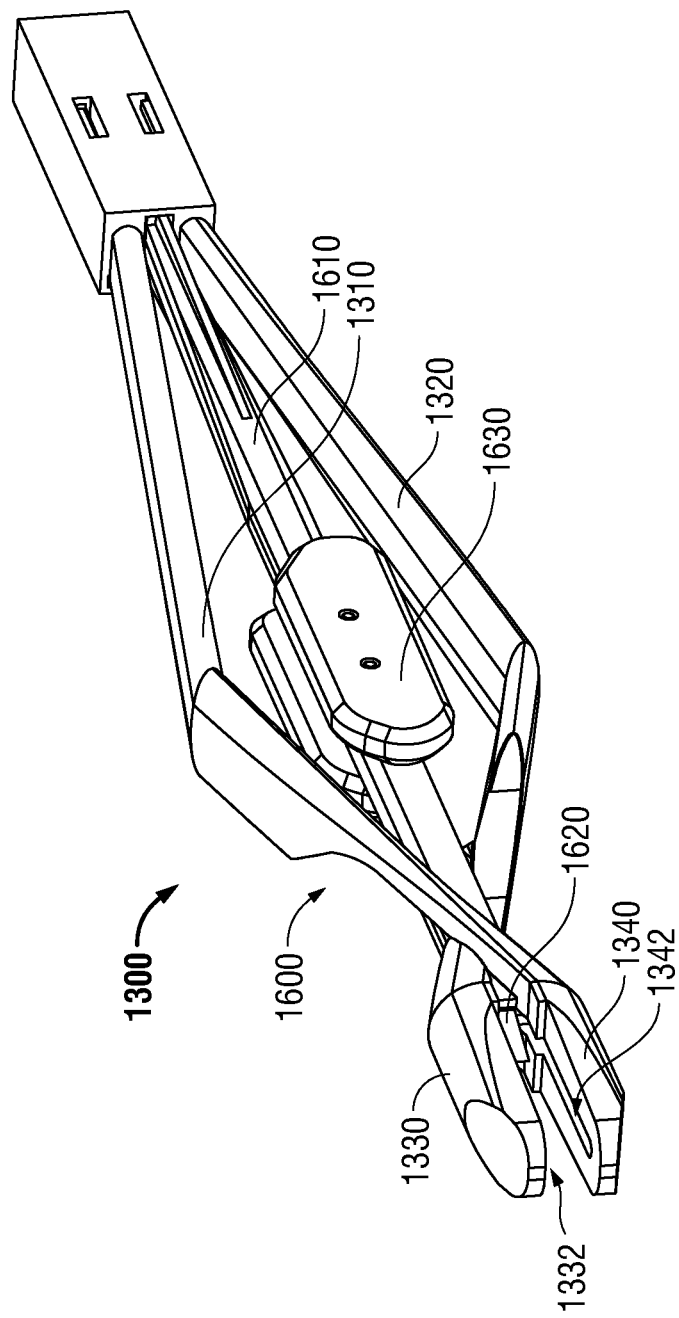
FIG. 11 is a perspective view of the electrosurgical pencil of FIG. 10 with a knife blade in a retracted position.
Figure 12:
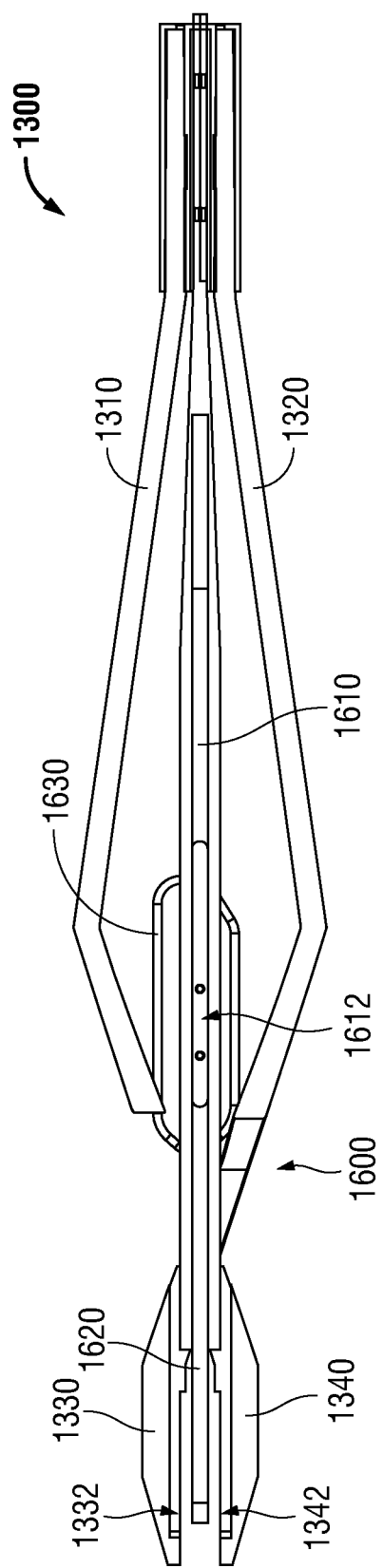
FIG. 12 is a side view of the electrosurgical pencil of FIG. 10.

FIGS. 10-12 show an alternate embodiment of a forceps 1300 that includes a knife blade assembly 1600. Forceps 1300 includes opposing shaft portions 1310 and 1320 that are mutually depressible to open the corresponding jaw members 1330 and 1340 for grasping tissue much in the same fashion as described above with respect to FIGS. 5 and 6. Knife blade assembly 1600 includes an elongated section 1610 disposed between body portions 1310, 1320, a knife 1620 retractable within elongated section 1610 and deployable between jaw members 1330, 1340 and a knife actuator 1630 disposed on elongated section 1610 and selectively advanceable to actuate knife 1620 between a retracted position and a deployed position. Jaw members 1330 and 1340 may include knife slots 1332 and 1342 defined therealong dimensioned to reciprocate knife 1620 upon actuation thereof. Knife 1620 may be a regular cutting blade or may alternatively be electrically connected to generator "G" such that knife 1620 is capable of electrosurgically cutting tissue. Knife 1620 is actuatable between the retracted position and the deployed position through actuation of knife actuator 1630 proximally and distally along slot 1612 defined in elongated section 1610. Knife 1620 may automatically retract when jaw members 1330, 1340 are disposed in the first, open position, as discussed above.

In use, knife 1620 is initially in the retracted position and jaw members 1330 and 1340 are biased toward the second, closed position. A surgeon first actuates opposing shaft portions 1310 and 1320 to transition jaw members 1330 and 1340 to the first, open position and places tissue between jaw member 1330 and 1340 before releasing shaft portions 1310 and 1320 to clamp the tissue therebetween. After tissue has been clamped between jaw members 1330 and 1340, the surgeon activates knife 1620 by translating knife actuator 1630 distally along slot 1612. As knife actuator 1630 is translated distally, knife 1620 also translates distally thereby cutting through tissue clamped between jaw members 1330 and 1340. Alternatively, knife 1620 itself may be supplied with electrosurgical energy to enhance the cutting effect. Once the tissue is cut the surgeon translates knife actuator 1630 proximally along slot 1612 to retract knife 1620 along elongated section 1610. A spring (not shown) may be included to release knife actuator 1630 to allow knife 1620 to automatically retract. In use, the forceps 1300 is initially biased with the jaw member 1330 and 1340 in the second, closed position which allows the surgeon to treat tissue with monopolar energy similar to an electrosurgical pencil. Electrosurgical energy is transmitted to the tissue from one or both jaw members 1330, 1340, and through the tissue to a return electrode or pad. During surgery, the surgeon has the option of opening jaw members 1330 and 1340 to receive and clamp tissue disposed therebetween, similar to a forceps, and to treat the tissue clamped therebetween with bipolar energy. The surgeon can then deploy the knife 1620 to cut the tissue after a seal is formed.

Figure 13A:
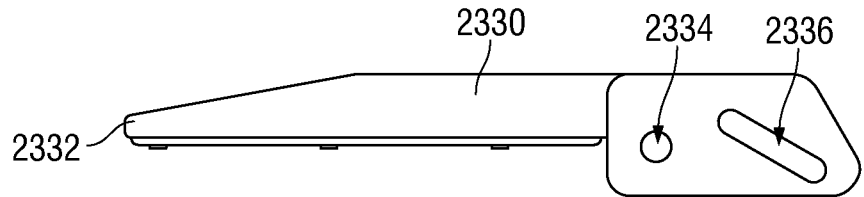
FIG. 13A is a side view of a first jaw member in accordance with an alternate embodiment of the jaw assembly of the present disclosure.
Figure 13B:
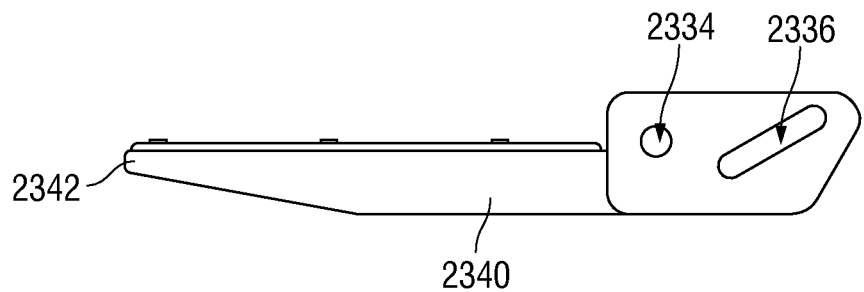
FIG. 13B is a side view of a second jaw member in accordance with the jaw assembly of FIG. 13A.
Figure 13C:
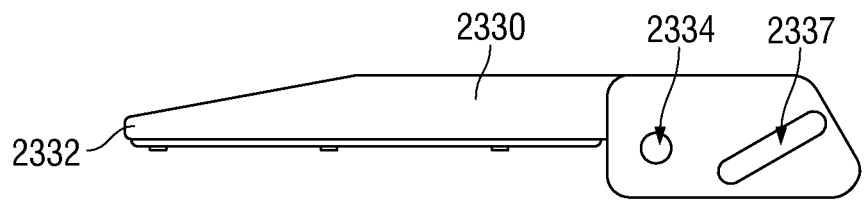
FIG. 13C is a side view of an alternate embodiment of the first jaw member of FIG. 13A.
Figure 13D:
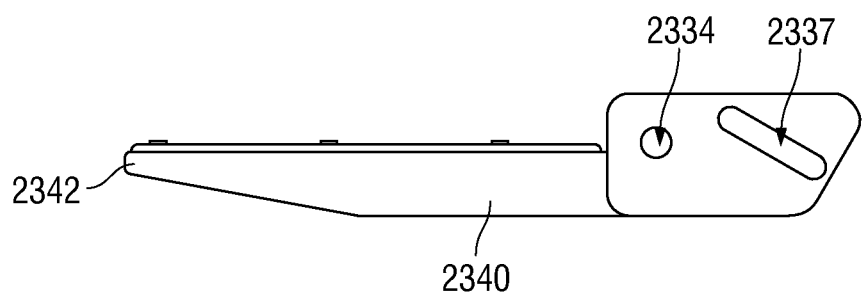
FIG. 13D is a side view an alternate embodiment of the second jaw member of FIG. 13B.
Figure 14:
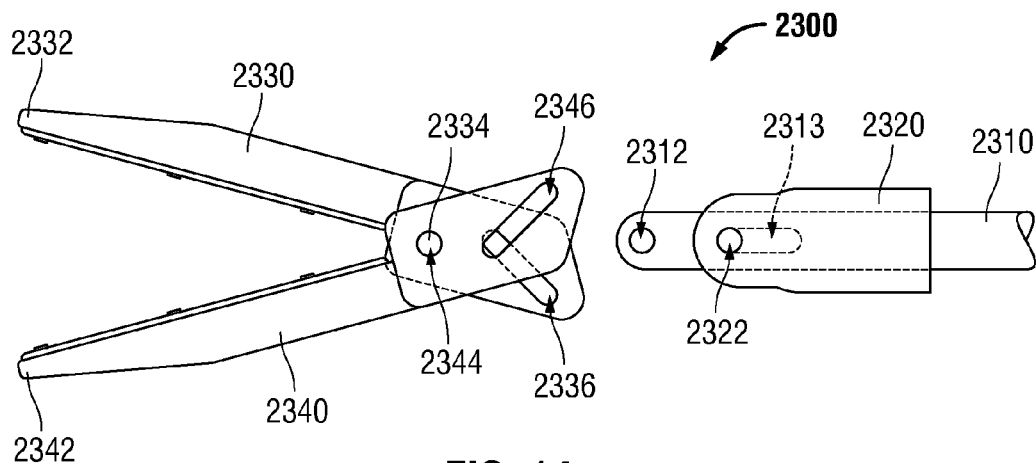
FIG. 14 is a side view of the jaw assembly of the embodiment of FIG. 13A.
Figure 15:
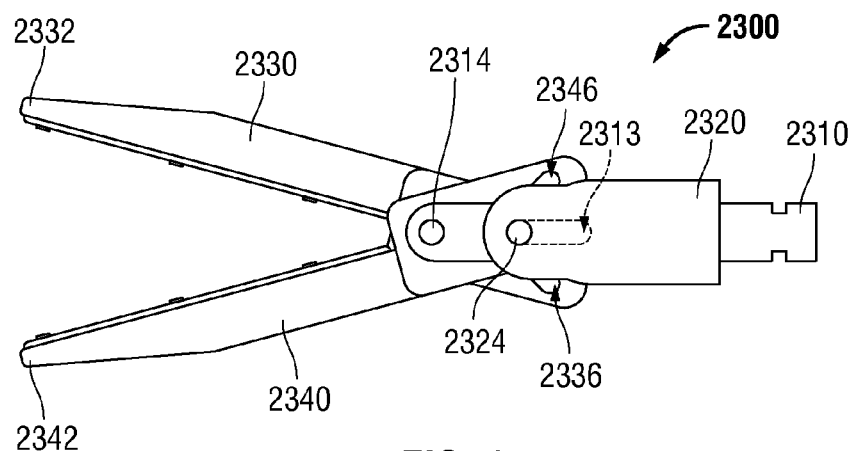
FIG. 15 is a side view of the jaw assembly of FIG. 14 with the jaw members in the first, open position.
Figure 16:
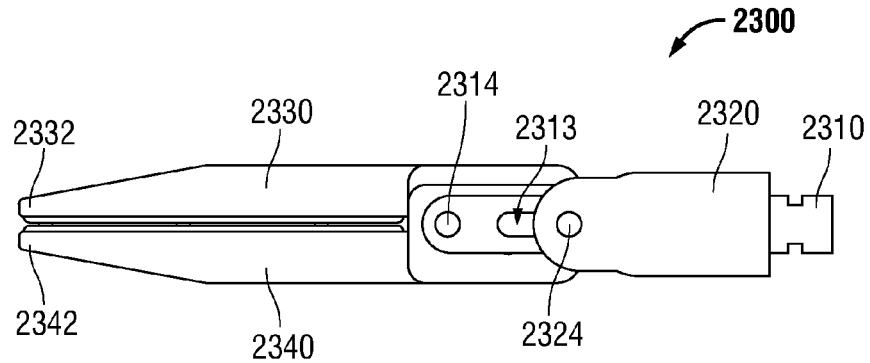
FIG. 16 is a side view of the jaw assembly of FIG. 14 with the jaw members in the second, closed position.
Figure 17:
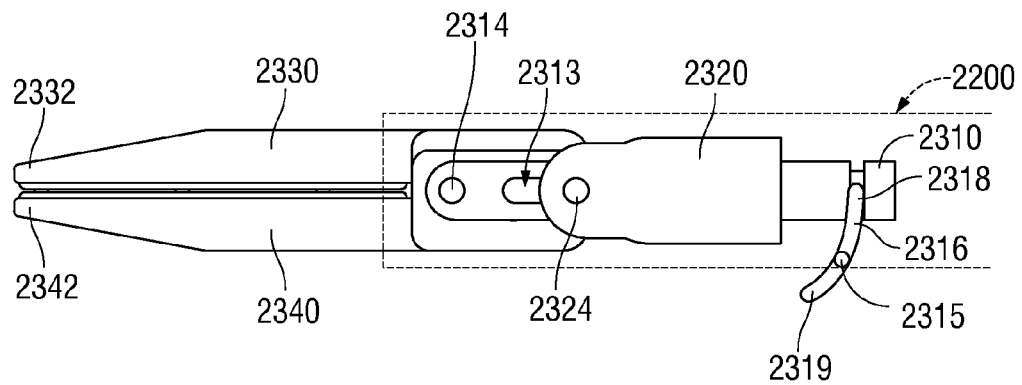
FIG. 17 is a side view of an alternate embodiment of the jaw assembly of FIG. 14 including a lever attached to an inner shaft thereof.

Referring now to FIGS. 14-16, jaw assembly 2300 includes an inner shaft 2310, an outer shaft 2320 and jaw members 2330, 2340. Each of jaw members 2330, 2340 includes a respective pivot hole 2334, 2344 and a respective slot 2336, 2346 (See also FIGS. 13A-13B). In this embodiment jaw members 2330, 2340 are removably attachable to inner and outer shafts 2310, 2320. Inner shaft 2310 and outer shaft 2320 each define a pin hole 2312 and 2322, respectively, for the reception of pins 2314, 2324 (FIG. 14). Inner shaft 2310 further includes a slot 2313 adapted for the receipt of pin 2324. As seen in FIG. 15, Jaw members 2330, 2340 are attached to inner shaft 2310 by pin 2314 inserted through pivot holes 2334, 2344 and pin hole 2312. Jaw members 2330, 2340 are also attached to outer shaft 2320 by pin 2324 inserted through slots 2313, 2336 and 2346 and pin hole 2322. Inner shaft 2310 and outer shaft 2320 are translatable relative to one another to slide pin 2324 along slots 2313, 2336 and 2346 to thereby actuate jaw members 2330, 2340 between the first, open and second, closed positions. For example, as seen in FIG. 16, translating inner shaft 2310 distally relative to outer shaft 2320 actuates jaw members 2330, 2340 from the first, open position to the second, closed position (e.g. approximating distal portions 2332, 2342 of jaw members 2330, 2340). Likewise, as seen in FIG. 15, translating inner shaft 2310 proximally relative to outer shaft 2320 actuates jaw members 2330, 2340 from the second, closed position to the first, open position (e.g. increases the spacing between distal portions 2332, 2342 of jaw members 2330, 2340). Jaw members 2330, 2340 are actuated due to the shape of slots 2336, 2346 (FIGS. 13A and 13B) where pin 2324 slides along slots 2336, 2346 during translation of inner shaft 2310 proximally or distally to thereby actuate jaw members 2330, 2340. Jaw members 2330 and 2340 may instead include slots 2337, 2347 (FIGS. 13C and 13D) which are dimensioned such that translating inner shaft 2310 distally will instead actuate jaw members 2330, 2340 from the second, closed position to the first, open position and that moving inner shaft 2310 proximally will actuate jaw members 2330, 2340 from the first, open position to the second, closed position. It is further contemplated that the surgeon may translate outer shaft 2320 instead of the inner shaft 2310 to actuate jaw members 2330, 2340 or that both shafts 2310, 2320 may be translated simultaneously relative to one another. Outer shaft 2320 may also be fixed to housing 2200.

During use, when a surgeon wishes to use a bipolar mode, the surgeon translates inner shaft 2310 proximally to transition jaw members 2330 and 2340 from the second, closed position to the first, open position (e.g. increasing the spacing between jaw members 2330 and 2340). Once jaw members 2330 and 2340 are in the first, open position the surgeon places tissue between jaw members 2330 and 2340 and translates inner shaft 2310 distally, thereby approximating jaw members 2330 and 2340 and clamping the tissue. Electrosurgical energy may then be applied as described below.

FIGS. 17-22 show an inner shaft 2310 that includes one or more levers 2316 attached at a fulcrum point 2318 for assisting in opening jaw members 2330, 2340. Lever 2316 may extend through housing 2200 and may be pivotably mounted to housing 2200 at a pivot point 2315 such that when a physician actuates lever 2316 at an end 2319, lever 2316 pivots about pivot point 2315 and applies force to inner shaft 2310 at fulcrum point 2318 for opening and closing jaw members 2330 and 2340. Lever 2316 allows a physician to generate additional force at fulcrum point 2318 for opening jaw members 2330, 2340.

In addition jaw assembly 2300 may include a leaf spring 2370 (FIGS. 20-21) attached to end 2319 of lever 2316 at its distal end and attached to outer shaft 2320 at its proximal end. Leaf spring 2370 is used to generate closing or clamping force for jaw members 2330, 2340 and includes leaf spring members 2372 and 2374 which may be utilized similar to actuators 350 and 360 of the embodiment shown in FIGS. 5 and 6. For example, as a physician exerts or removes pressure on leaf spring members 2372 and 2374, jaw members 2330 and 2340 are transitioned between the first, open and second, closed positions due to actuation of end 2319 of lever 2316 by leaf spring 2370.

Figure 22:
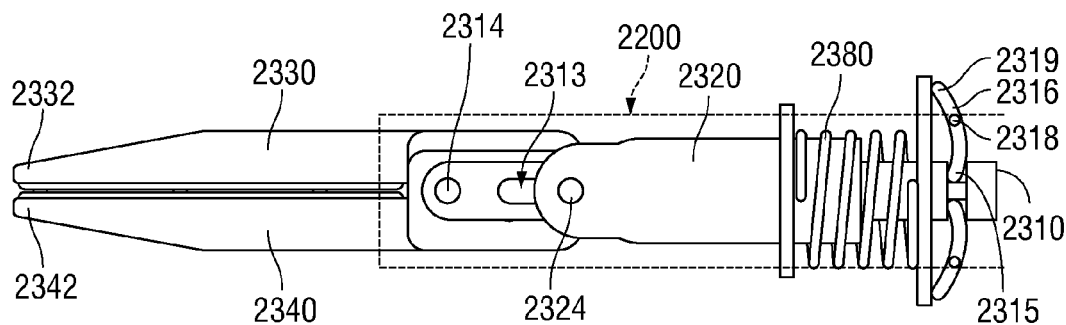
FIG. 22 is a side view of an alternate embodiment of the jaw assembly of FIG. 19 with the levers biased by a spring.

In another embodiment, shown in FIG. 22, a compression spring 2380 is disposed around outer shaft 2320 and attached to ends 2319 of the one or more levers 2316 to provide additional closing force to jaw members 2330, 2340 through mechanical action at fulcrum point 2318. Electrosurgical pencil 100 may utilize one or more of these features at the same time. For example, levers 2316 may be included in conjunction with either leaf spring 2370 or compression spring 2380. In addition electrosurgical pencil 100 may include both leaf spring 2370 and compression spring 2380 as desired.

Figure 18:
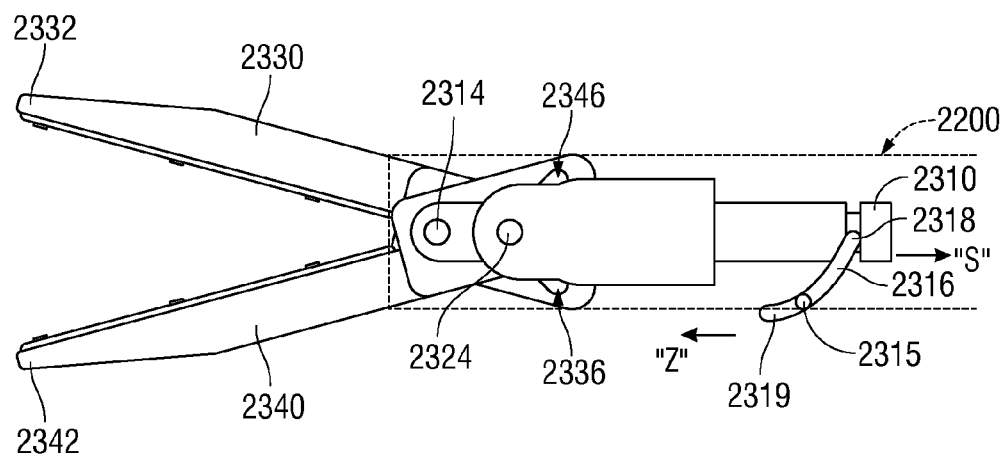
FIG. 18 is a side view of the jaw assembly of FIG. 17 with the jaw members in the first, open position.
Figure 19:
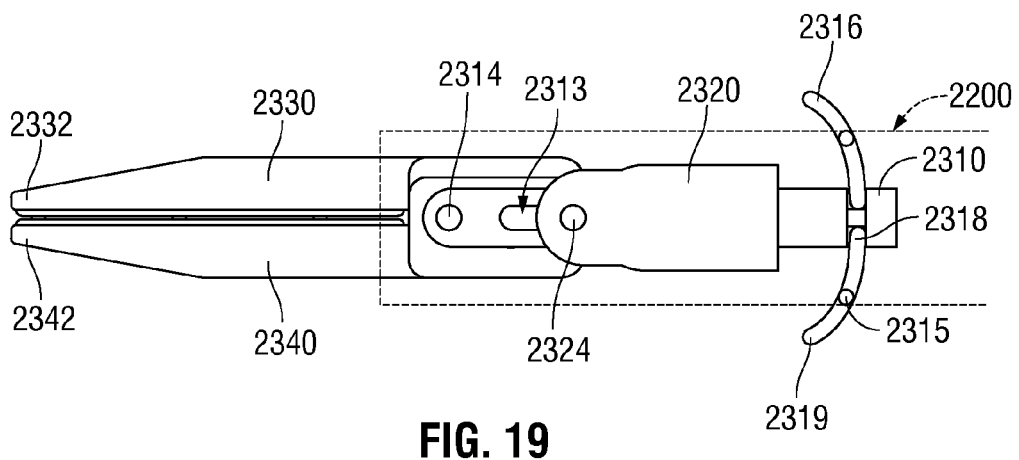
FIG. 19 is a side view of the jaw assembly of FIG. 17 including two levers attached to the inner shaft.
Figure 20:
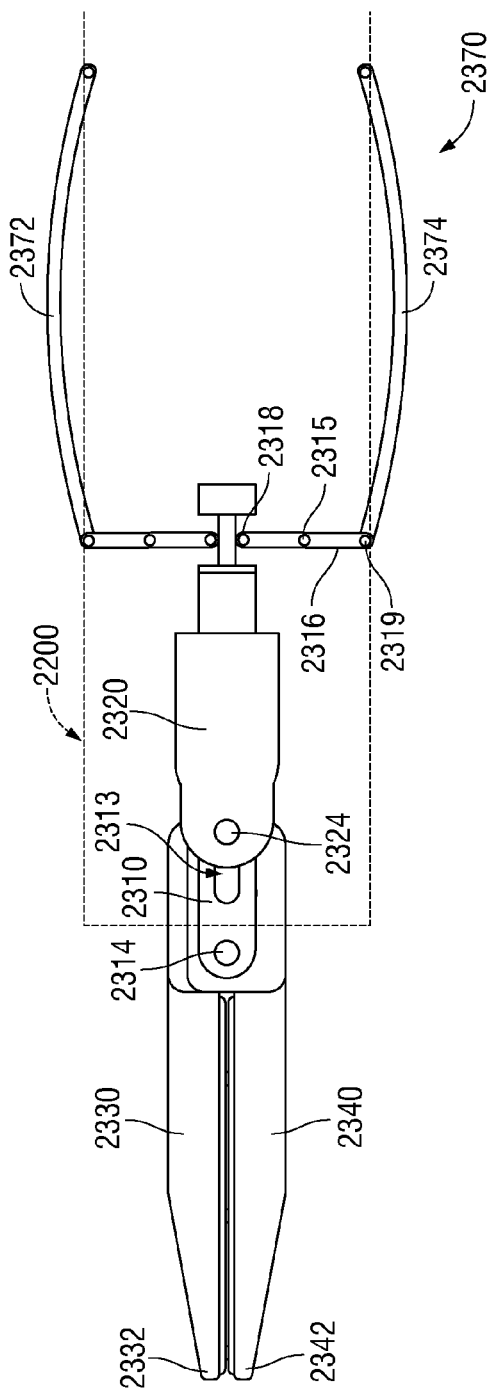
FIG. 20 is a side view of the jaw assembly of FIG. 19 including leaf springs attached to the ends of the levers and to the housing with the jaw members in the second, closed position.
Figure 21:
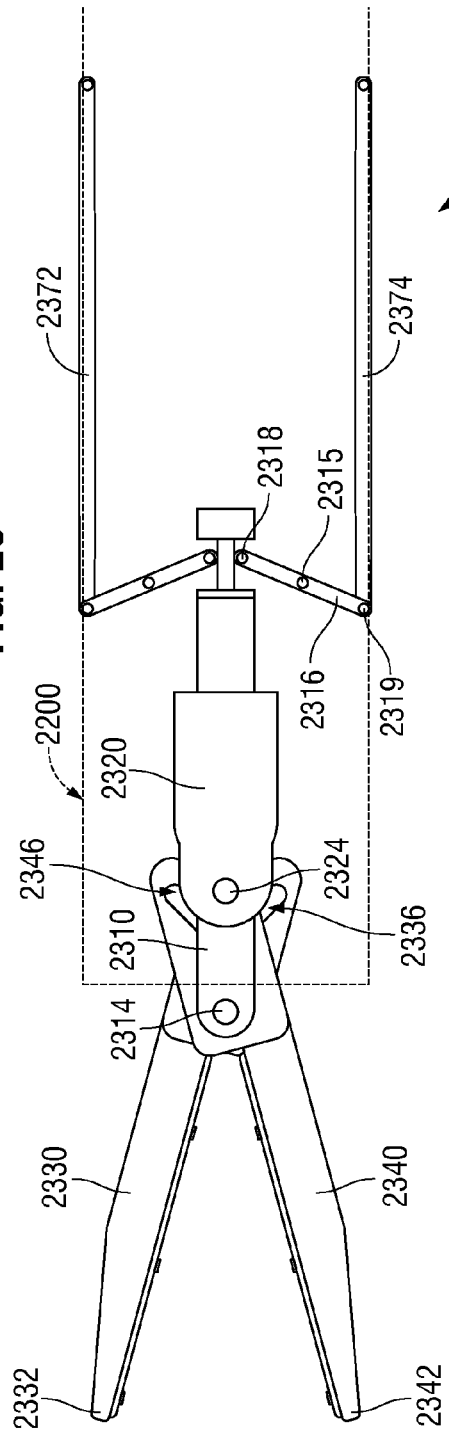
FIG. 21 is a side view of the jaw assembly of FIG. 20 with the jaw members in the first, open position.

During use, and as shown in FIGS. 18-19, the surgeon actuates end 2319 of lever 2316 in a direction "Z" which applies force on inner shaft 2310 at fulcrum point 2318 in a proximal direction "S". This forces inner shaft 2310 to translate proximally and thereby transition jaw members 2330, 2340 from the second, closed position to the first, open position (e.g. spaced further apart). Once tissue is placed between jaw member 2330 and 2340 the surgeon actuates end 2319 of level 2316 in a direction opposite to "Z" which applies force on inner shaft 2310 at fulcrum point 2318 in a distal direction opposite to "S". This forces inner shaft 2310 to translate distally and thereby transition jaw members 2330, 2340 from the first, open position toward the second, closed position thereby clamping the tissue therebetween.

Electrosurgical energy may then be applied to the tissue as discussed below. The use of leaf spring 2370 or coil spring 2380 provides a biasing force on lever 2316 and inner shaft 2310 such that when the physician releases lever 2316 or removes pressure from leaf spring members 2372 and 2374, inner shaft 2310 automatically translates distally to transition jaw members 2330 and 2340 toward the second, closed position for clamping tissue therebetween. The leaf spring 2370 and/or the compression spring 2380 are utilized to generate the appropriate closure pressure on the tissue to effect a tissue seal (e.g., about 3 kg/cm$^2$ to about 16 kg/cm$^2$).

Figure 23:
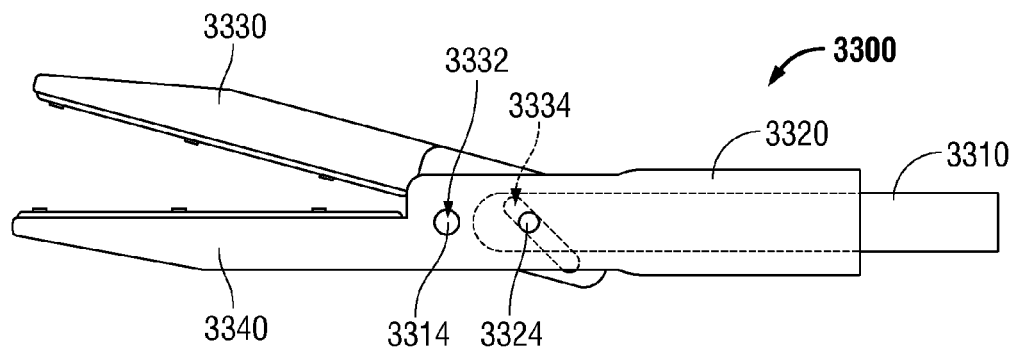
FIG. 23 is a side view of an alternate embodiment of the jaw assembly of FIG. 14 where only the first jaw is actuatable and the jaw members are in the first, open position.
Figure 24:
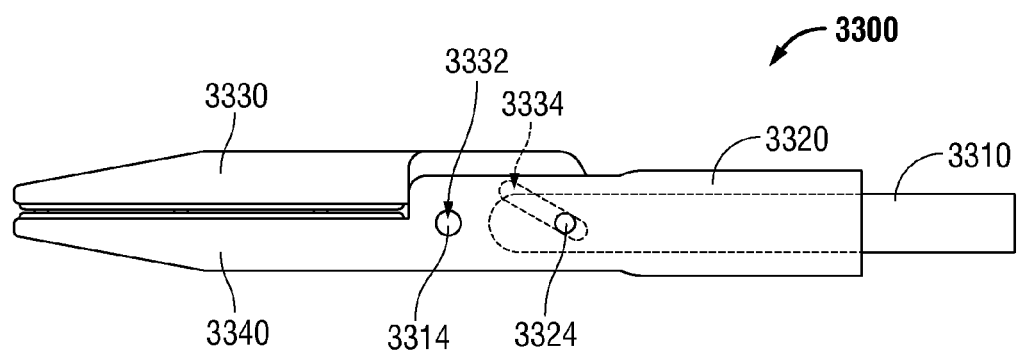
FIG. 24 is a side view of the jaw assembly of FIG. 23 with the jaw members in the second, closed position.

Referring now to FIGS. 23-24, another embodiment of a jaw assembly 3300 is disclosed where only jaw member 3330 is actuatable while jaw member 3340 is rigidly fixed in place. Moving inner shaft 3310 proximally and distally only transitions jaw member 3330 between the first, open and second, closed positions while jaw member 3340 remains stationary. In this embodiment jaw member 3330 includes a pivot hole 3332 and a slot 3334 as described in previous embodiments while jaw 3340 is rigidly fixed to outer shaft 3320. Jaw member 3340 and outer shaft 3320 may be monolithically formed. Jaw member 3330 is attached to outer shaft 3320 by pin 3314 inserted through pivot hole 3332 and is attached to inner shaft 3310 by pin 3324 inserted through slot 3334.

In yet another embodiment of the present disclosure, as shown in FIGS. 25-27, a rotating wheel 4250 is disposed at a distal end 4210 of housing 4200 and actuatable to adjust the rotational angle of jaw members 4330, 4340 to a desired alignment. As seen in FIGS. 26 and 27, jaw members 4330 and 4340 are transitionable between at least a first configuration (FIG. 26) and a second configuration (FIG. 27) upon actuation of rotating wheel 4250 in a clockwise or counter-clockwise direction. Rotating wheel 4250 and thus jaw members 4330 and 4340 may be rotated a full 360° thereby allowing for a plurality of different configurations in addition to the first and second configurations. During use, a surgeon utilizes surgical pencil 4100 as described above in previous embodiments and may additionally actuate rotating wheel 4250 in a clockwise or counter-clockwise direction until the desired configuration of jaw members 4330 and 4340 is achieved.

Figure 28:
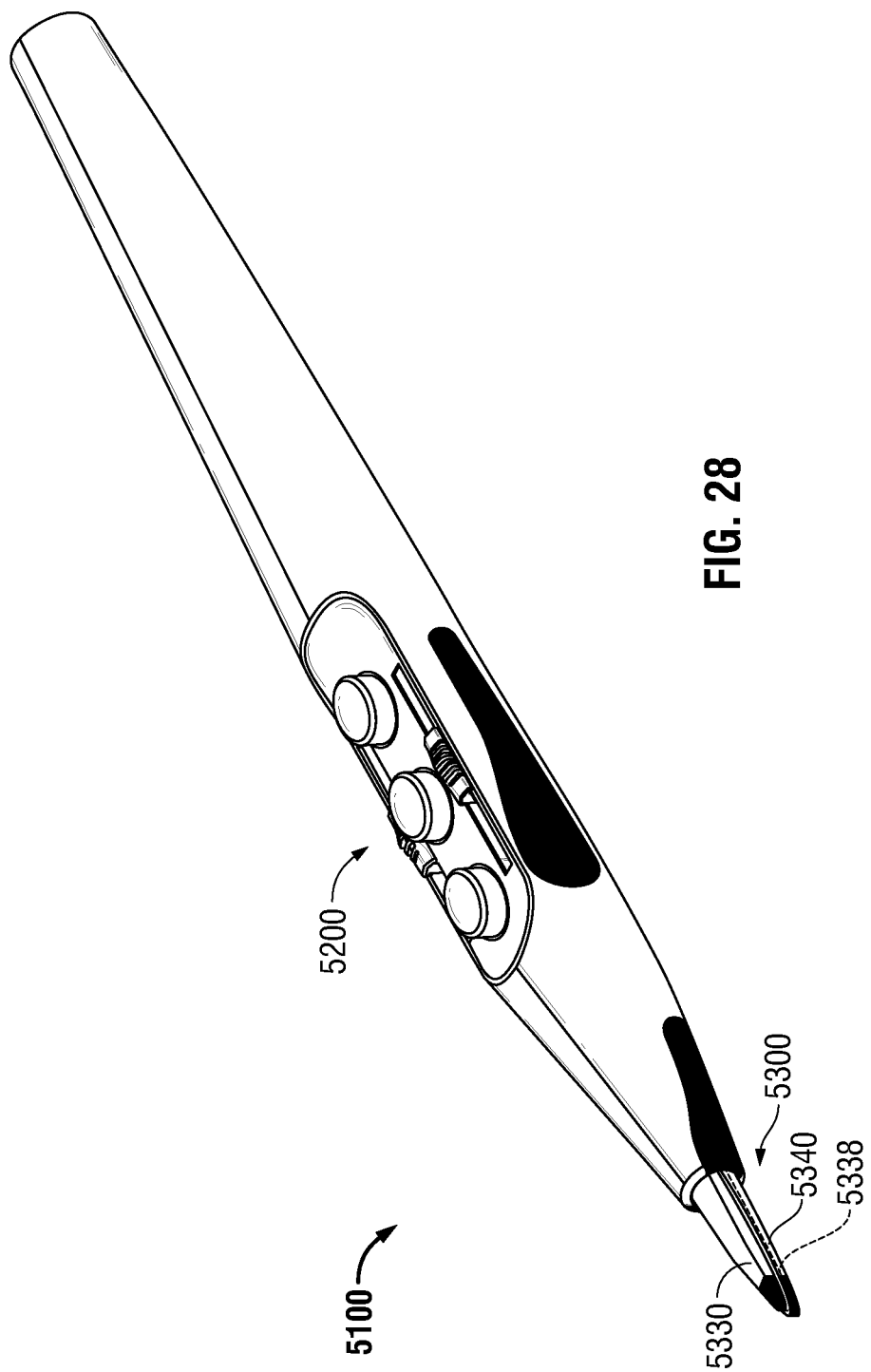
FIG. 28 is a perspective view of an electrosurgical pencil in accordance with another embodiment of the present disclosure wherein the jaw members have a clamshell arrangement.
Figure 29:
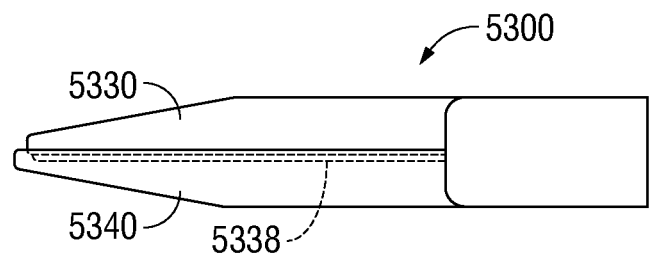
FIG. 29 is a side view of the jaw members of the electrosurgical pencil of FIG. 28 when in the second, closed position.

In yet another embodiment of the present disclosure, as shown in FIGS. 28-29, jaw assembly 5300 includes jaw members 5330, 5340 where jaw member 5330 defines a cavity or depression 5338 dimensioned for the reception of jaw member 5340 in a clam shell type configuration. This allows jaw member 5330 to be used in monopolar mode while keeping the jaw member 5340 isolated therefrom.

Figure 30:
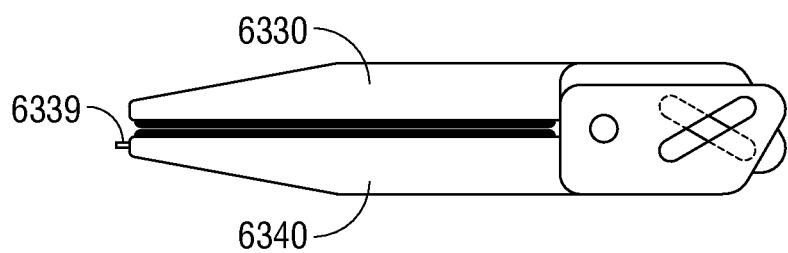
FIG. 30 is a side view of an alternate embodiment of the jaw members of FIGS. 13A and 13B including a selectively-extendable electrode tip.
Figure 31:
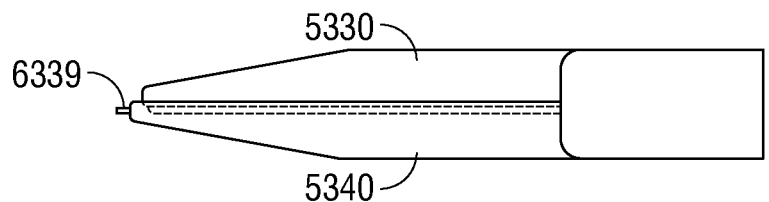
FIG. 31 is a side view of an alternate embodiment of the jaw members of FIG. 28 including a selectively-extendable electrode tip.

FIGS. 30-31 show jaw members 6330 and 6340 including an extended electrode tip 6339 for use during monopolar electrosurgery. Extended electrode tip 6339 allows a surgeon to apply monopolar energy to a target site while keeping jaw members 6330 and 6340 from contacting the tissue. Electrode tip 6339 may be attached to jaw member 5330 or jaw member 5340 of the clam shell embodiment disclosed above, as seen in FIG. 31.

Figure 32:
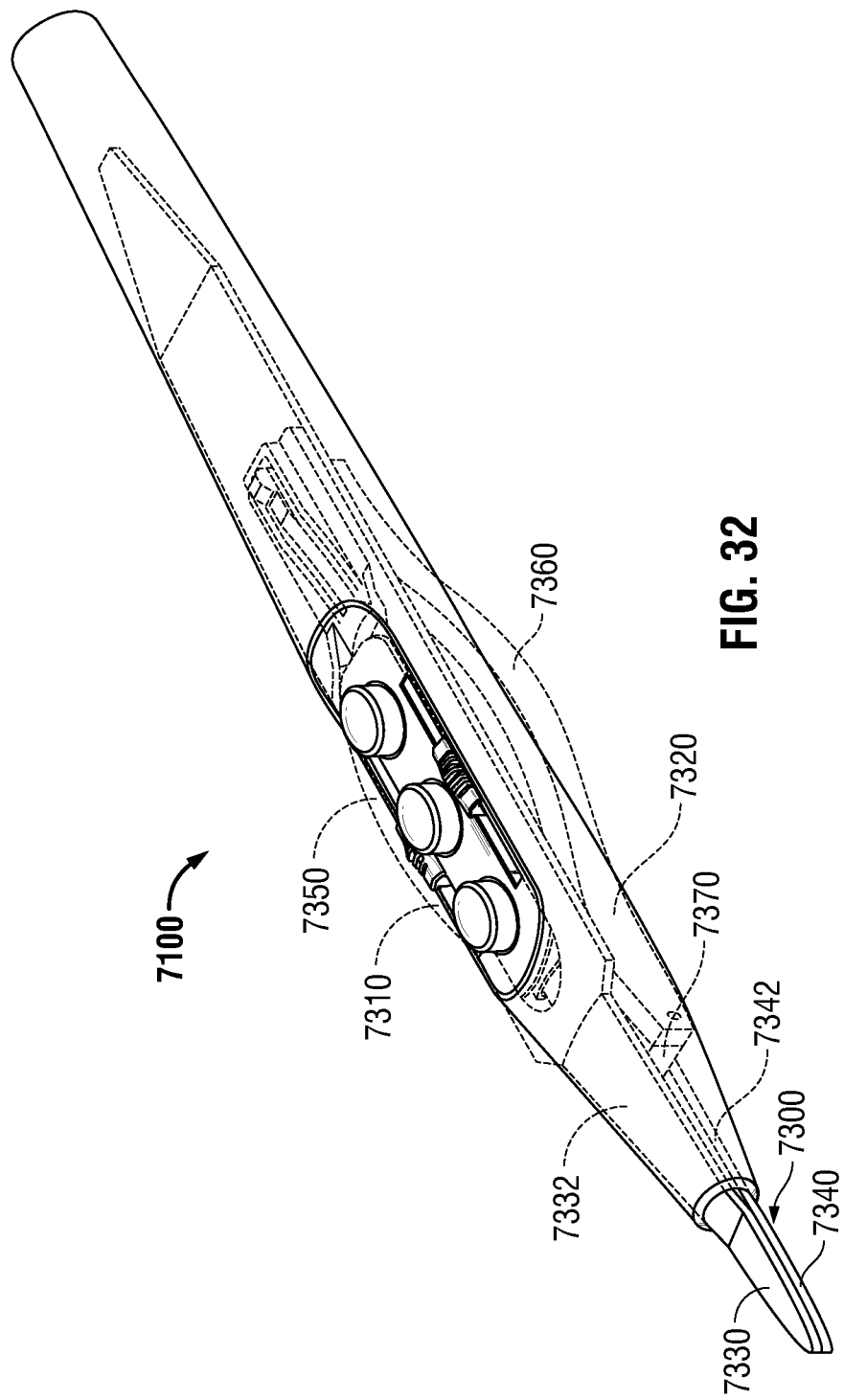
FIG. 32 is a perspective view of an electrosurgical pencil according to an alternate embodiment of the present disclosure including wedge actuated jaw members.
Figure 33:
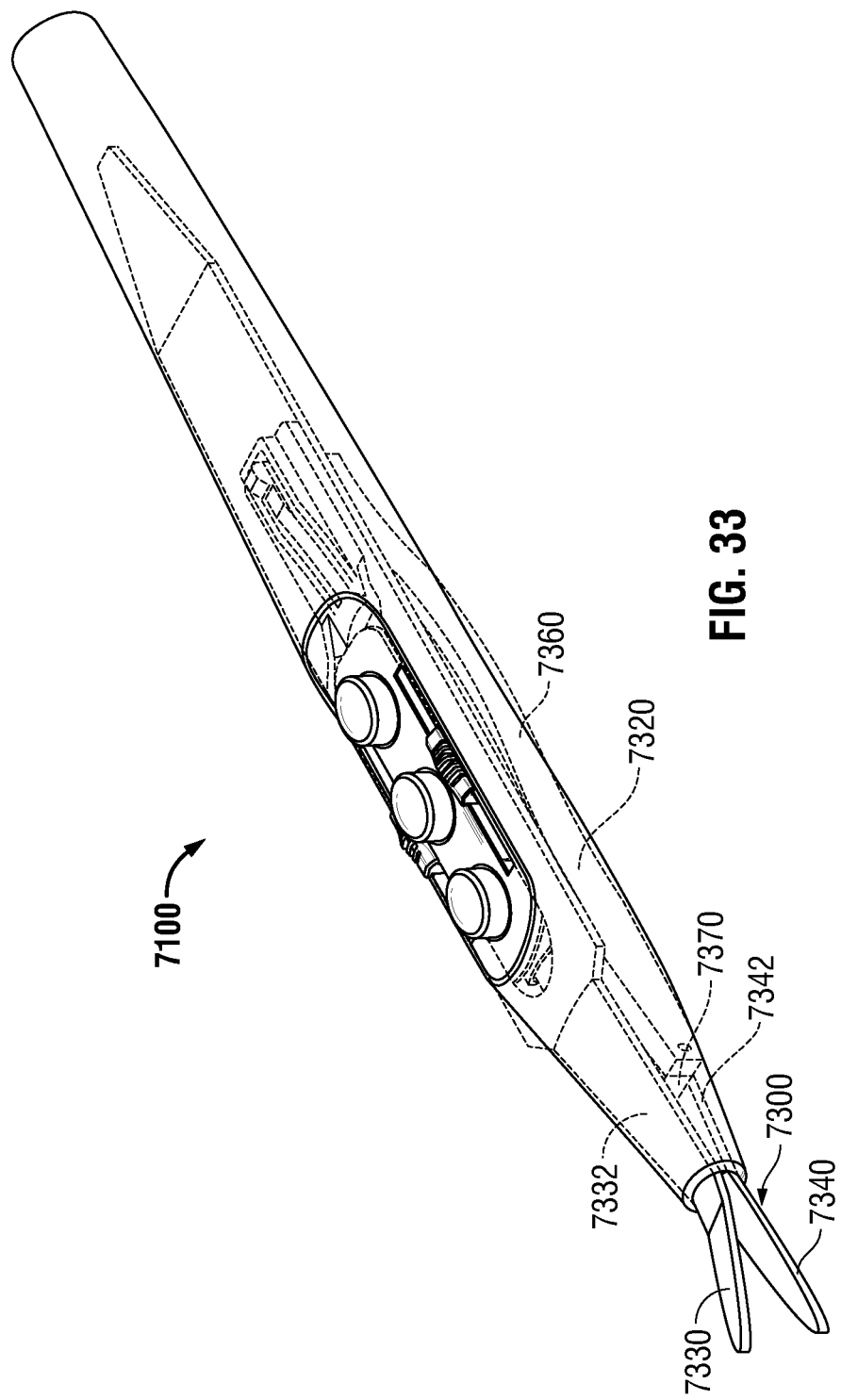
FIG. 33 is a perspective view of the electrosurgical pencil of FIG. 32 with the jaw members in the first, open position.
Figure 34:
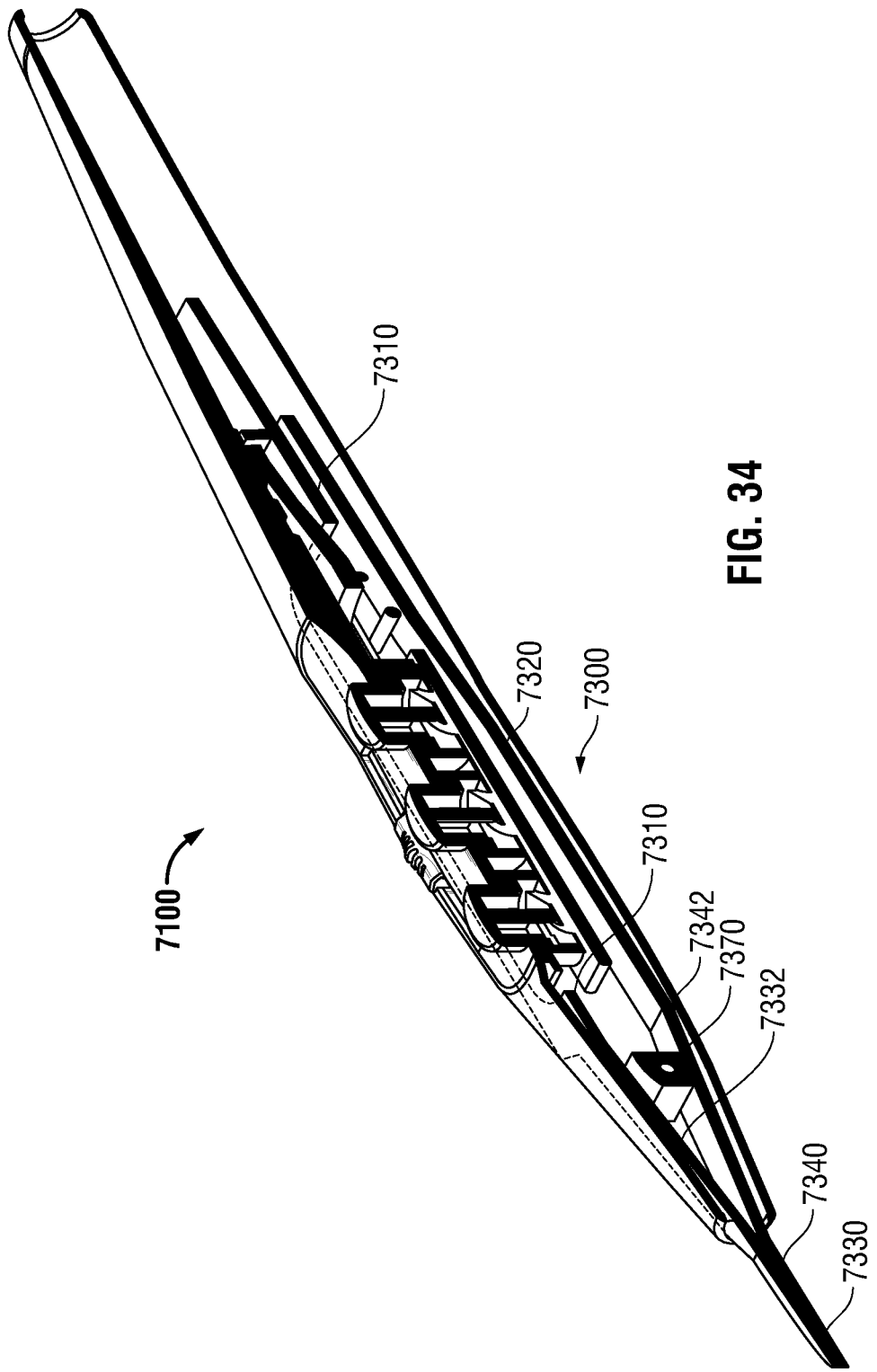
FIG. 34 is a side, cut-away view of the electrosurgical pencil of FIG. 32.

FIGS. 32-34 show a surgical pencil 7100 including a jaw assembly 7300 having body portions 7310 and 7320 separate from jaw members 7330 and 7340. Body portions 7310 and 7320 include actuators 7350 and 7360 and connect to a wedge 7370 disposed between jaw members 7330 and 7340. Actuation of actuators 7350 and 7360 translates body portions 7310 and 7320 relative to each other and thereby translates wedge 7370 proximally or distally between jaw members 7330 and 7340. In this embodiment jaw members 7330 and 7340 include sloped portions 7332, 7342 on which wedge 7370 rests. When wedge 7370 is translated in the distal direction, wedge 7370 slides along sloped portions 7332 and 7342 and forces jaw members 7330 and 7340 apart. In this way wedge 7370 is able to transition jaw members 7330 and 7340 between the first, open and second, closed positions. Jaw members 7330 and 7340 are biased toward the second, closed position such that when the surgeon stops actuating actuators 7350, 7360 jaw members 7330 and 7340 naturally force wedge 7370 proximally along sloped portions 7332 and 7342 and return to the second, closed position.

In use, a surgeon applies pressure on actuators 7350 and 7360 to actuate wedge 7370 distally. As wedge 7370 translates distally it slides along sloped portions 7332 and 7342 of jaw members 7330 and 7340 to transition jaw members 7330 and 7340 from the second, closed position to the first, open position (e.g. spaced further apart). The surgeon then places the desired tissue between jaw members 7330 and 7340 and releases the pressure on actuators 7350 and 7360. The biasing force of jaw members 7330 and 7340 forces wedge 7370 proximally to transition jaw members 7330 and 7340 from the first, open position back to the second, closed position, thereby clamping onto the tissue therebetween. Electrosurgical energy may then be applied to the tissue.

For the purposes herein, the terms "switch" or "switches" includes electrical actuators, mechanical actuators, electromechanical actuators (rotatable actuators, pivotable actuators, toggle-like actuators, buttons, etc.) or optical actuators.

With reference to FIGS. 1-4, 7-9 and 35-39 electrical assembly 400 includes one or more activation switches 410, 420 and 430 that extend through an opening 260 of housing 200. Activation switches 410, 420 and 430 are operatively supported on tactile elements 412, 422, 432 (shown as a snap-dome switch) provided on a switch plate 440 (See FIG. 39). Activation switches 410, 420 and 430 control the transmission of RF electrical energy supplied from generator "G" to jaw members 330 and 340. More particularly, switch plate 440 is positioned on top of a voltage divider network 450 (hereinafter "VDN 450") such that tactile elements 412, 422, 432 are operatively associated therewith. VDN 450 (e.g., here shown as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage.

Figure 7:
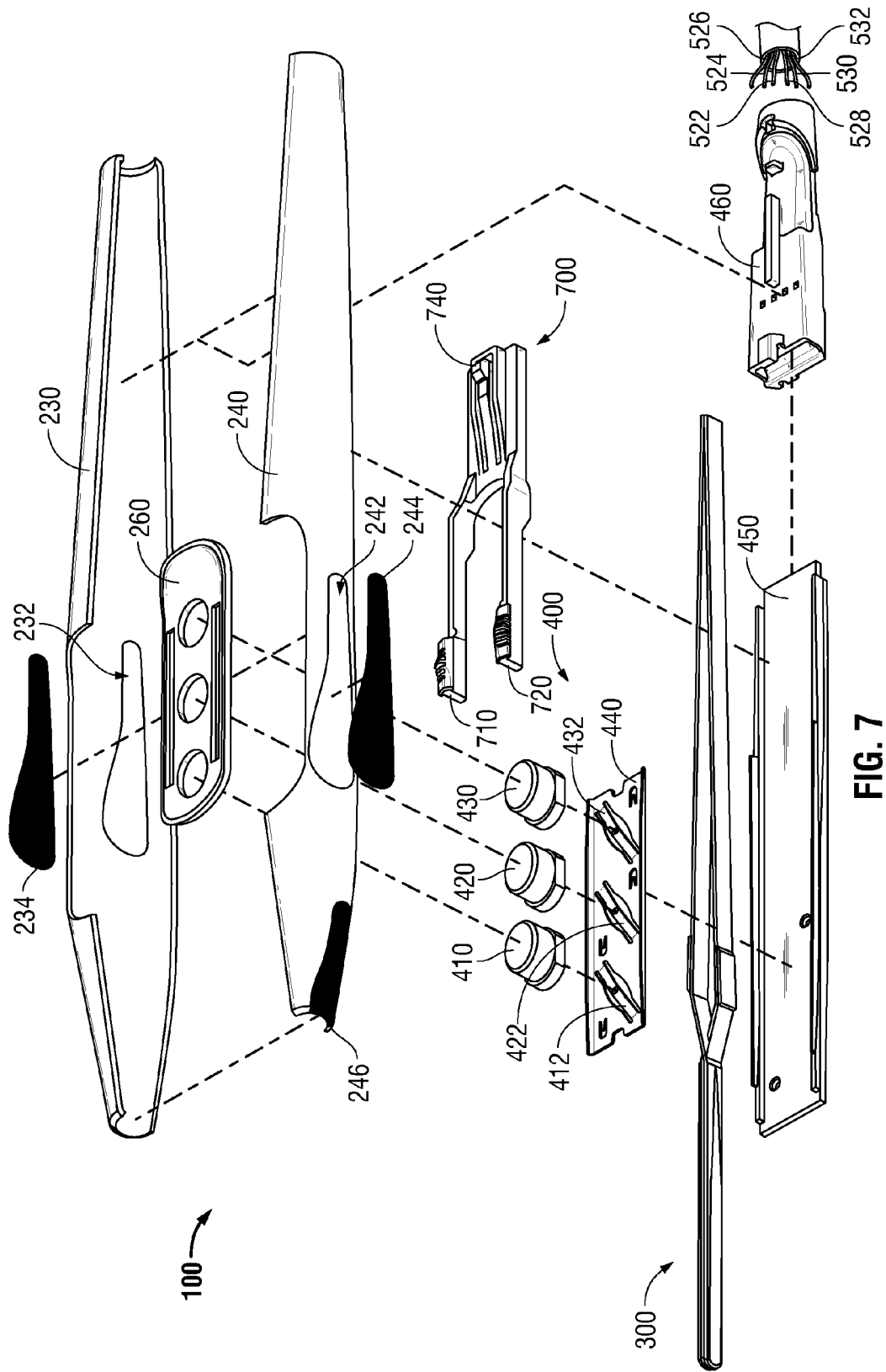
FIG. 7 is an exploded, perspective view of the electrosurgical pencil of FIG. 1.
Figure 35:
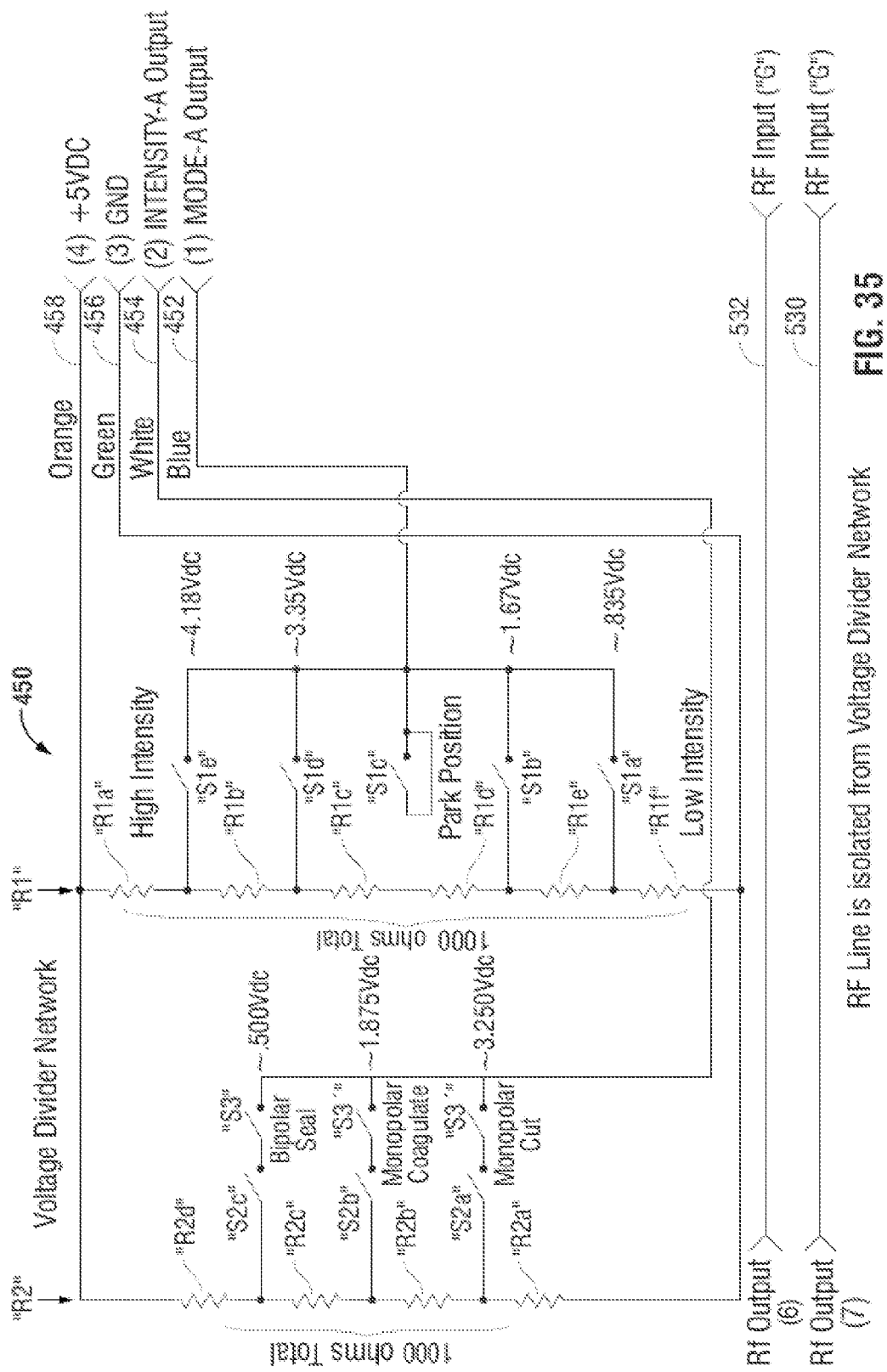
FIG. 35 is a schematic illustration of the voltage divider network of the present disclosure.
Figure 38:
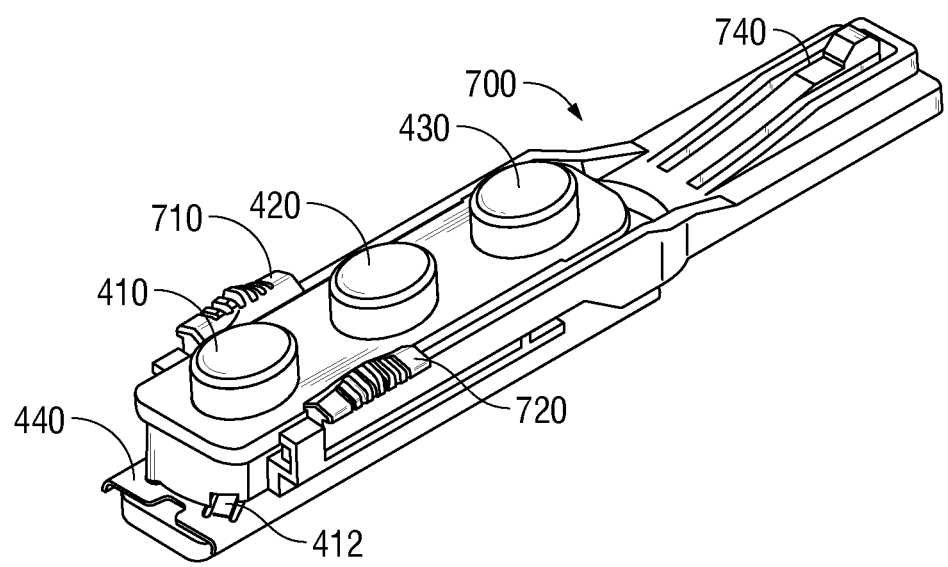
FIG. 38 is a perspective view of a portion of the electrical assembly of the surgical pencil of FIG. 1 including switches and an intensity controller.
Figure 39:
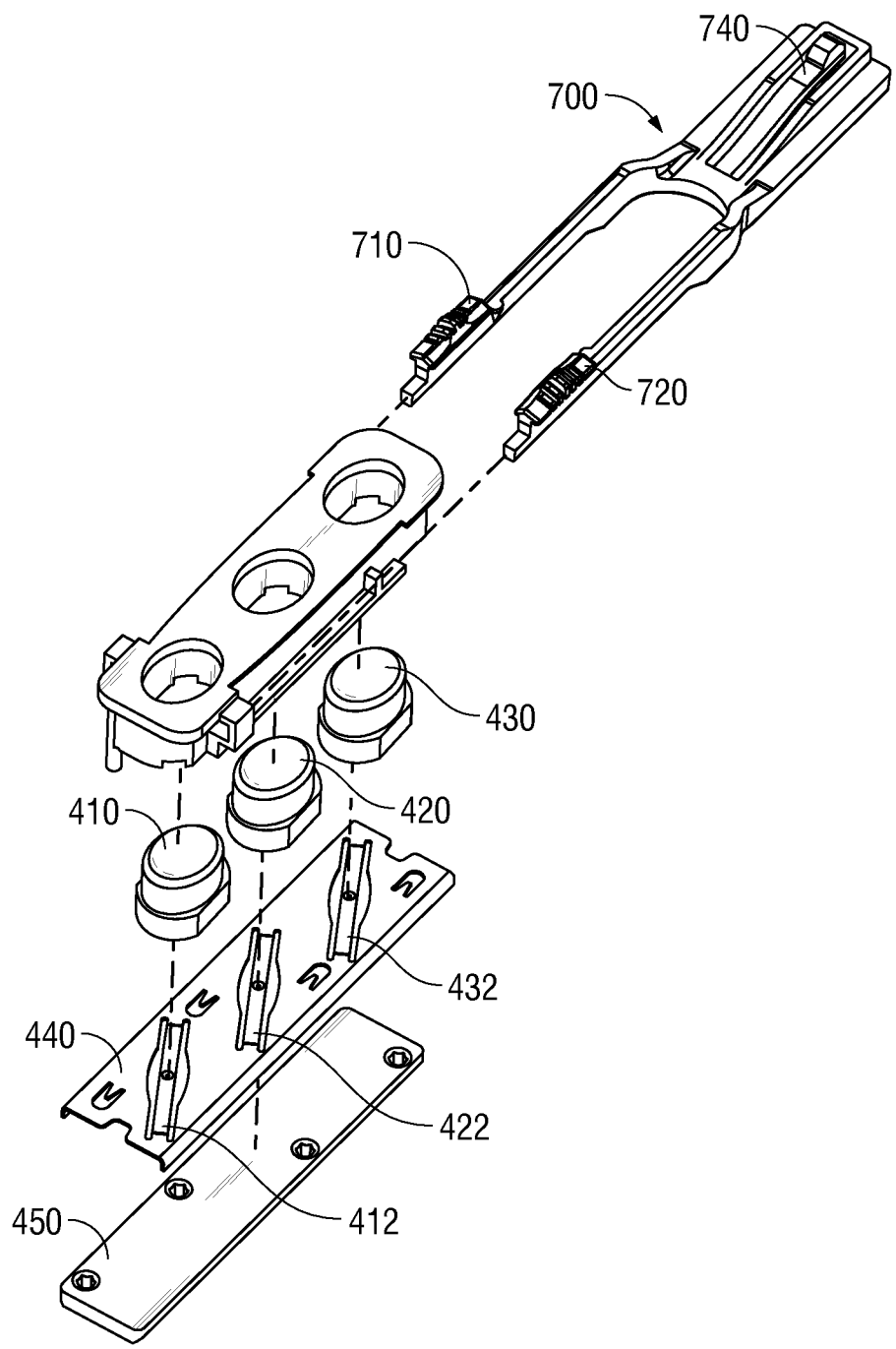
FIG. 39 is an exploded perspective view of the portion of the electrical assembly of FIG. 38.

In use, depending on which activation switch 410, 420 or 430 is depressed a respective tactile element 412, 422, 432 is pressed into contact with VDN 450 and a characteristic signal is transmitted to electrosurgical generator "G" via a cable 520 (FIGS. 1, 7, 35). Cable 520 may include one or more control wires 522, 524, 526, and 528, and two RF lines 530 and 532 (FIG. 7). Control wires 522, 524, 526 and 528 are preferably electrically connected to switches 410, 420 and 430 and intensity controller 700 via a controller terminal 460 (FIG. 7) which is operatively connected to VDN 450. By way of example only, electrosurgical generator "G" may be used in conjunction with the device wherein generator "G" includes a circuit for interpreting and responding to the VDN settings. It is also contemplated that electrosurgical energy may be supplied by a battery.

Activation switches 410, 420 and 430 are configured and adapted to control the mode and/or "waveform duty cycle" to achieve a desired surgical intent. For example, first activation switch 410 can be set to deliver a characteristic signal to electrosurgical generator "G" which in turn transmits a duty cycle and/or waveform shape that produces a cutting and/or dissecting effect/function. Meanwhile, second activation switch 420 can be set to deliver a characteristic signal to electrosurgical generator "G" which in turn transmits a duty cycle and/or waveform shape which produces a division or dividing with hemostatic effect/function. Finally, third activation switch 430 can be set to deliver a characteristic signal to electrosurgical generator "G" which in turn transmits a duty cycle and/or waveform shape which produces a hemostatic effect/function.

One of switches 410, 420 or 430 may be set to activate a monopolar mode and another of switches 410, 420 or 430 may be set to activate a bipolar mode or the same switch 410, 420 or 430 may be set to activate either a monopolar mode or a bipolar mode depending on which position jaw members 330 and 340 are situated. Safety switches "S3" and "S3'" (FIG. 35) as discussed above may be included to prevent bipolar activation when jaw members 330 and 340 are disposed in the second, closed position and monopolar activation when jaw members 330 and 340 are disposed in the first, open position. Safety switches "S3" and "S3'" may alternatively be a single switch where only one of bipolar and monopolar modes may be active at a given time depending on the position of the jaws. One switch 410, 420 or 430 may be depressed multiple times to cycle between a monopolar mode, a bipolar mode and a power "OFF" mode where no energy is provided to jaw members 330 and 340.

As seen in FIG. 35, RF lines 530 and 532 for transmitting RF energy to jaw members 330, 340 are electrically connected to jaw members 330 and 340 respectively. It is alternatively contemplated that RF lines 530 and 532 may be connected to body portions 310 and 320 where body portions 310 and 320 are in electrical communication with jaw member 330 and 340 respectively. Body portions 310 and 320 may also be insulated from one another. Each of jaw members 330, 340 receives a separate electrical connection from one of RF lines 530 and 532. It is also contemplated that both jaw members 330, 340 may receive an electrical connection from the same RF line 530, 532 during monopolar use. When RF lines 530 and 532 are directly connected to jaw members 330 and 340, RF lines 530 and 532 bypass VDN 450 and are isolated from VDN 450 and control wires 522, 524, 526 and 528. By directly connecting RF lines 530 and 532 to jaw members 330, 340 and isolating VDN 450 from the RF energy transmission, the electrosurgical current does not flow through VDN 450. This in turn, increases the longevity and life of VDN 450 and/or switches 410, 420 and 430.

As such, a VDN 450 and/or switches 410, 420, 430 may be selected which are less complex and/or which are relatively inexpensive since the switches do not have to transmit current during activation. For example, if RF wires 530 and 532 are provided, switches 410, 420, 430 may be constructed by printing conductive ink on a plastic film. On the other hand, if RF wires 530 and 532 are not provided, switches 410, 420, 430 may be of the type made of standard stamped metal which adds to the overall complexity and cost of the instrument.

With reference to FIG. 35, VDN 450 includes a first transmission line 452 to operate the various Modes of electrosurgical pencil 100; a second transmission line 454 to operate the various intensities of electrosurgical pencil 100; a third transmission line 456 to function as a ground for VDN 450; and a fourth transmission line 458 which may transmit up to about +5 volts to VDN 450. Each of the first, second, third, and fourth transmission lines is electrically connected to one of control wires 522, 524, 526, and 528 via controller terminal 460 and thus is electrically connected to generator "G".

VDN 450 includes a first variable resistor "R1" having a maximum resistance of 2000 ohms. First resistor "R1" is a variable resistor which is represented in FIG. 35 as six (6) individual resistors "R1a-R1f" connected between third transmission line 456 and fourth transmission line 458. Each resistor "R1a-R1f" of the first set of resistors has a resistance of 333 ohms. First resistor "R1" is selectively actuatable by intensity controller 700 at a plurality of locations along the length thereof. The locations along the length of the first resistor "R1" correspond to the detents 290 formed along the inner upper surface of side shell portions 230, 240. (see FIGS. 8 and 36) These locations along the length of resistor "R1" are represented as a first set of switches "S1a-S1e". In operation, as intensity controller 700 is translated along first resistor "R1" the value of the resistance of first resistor "R1" is changed. The change of the resistance value of first resistor "R1" is represented in FIG. 35 as the closing of a switch "S1a-S1e". The change in resistance of first resistor "R1" causes a change in voltage along second transmission line 454 which is measured by electrosurgical generator "G" which, in turn, transmits an RF energy at a unique intensity to electrosurgical pencil 100.

When intensity controller 700 is translated to a third, middle position along first resistor "R1", corresponding to switch "S1c", a "park position" is established in which no resistance is present. Accordingly, electrosurgical generator "G" measures a maximum voltage value of zero volts.

VDN 450 further includes a second variable resistor "R2" having a maximum resistance of 2000 ohms. Second resistor "R2" is represented in FIG. 35 as four (4) individual resistors "R2a-R2d" connected between third transmission line 456, and fourth transmission line 458. Resistor "R2a" has a resistance of 200 ohms, resistor "R2b" has a resistance of 550 ohms, resistor "R2c" has a resistance of 550 ohms, and resistor "R2d" has a resistance of 700 ohms.

Second resistor "R2" is selectively actuatable by any one of activation switches 410, 420 and 430. The location where second resistor "R2" is actuated by an activation switch 410, 420 or 430 is represented as a second set of switches "S2a-S2c". In operation, depending on which switch "S2a-S2c" of the second set of switches "S2" is closed, by actuation of a particular activation switch 410, 420 or 430, the value of the resistance of second resistor "R2" is changed. The change of the resistance value of second resistor "R2" causes a change in voltage along first transmission line 452 which is measured by electrosurgical generator "G" which, in turn, activates and transmits a different mode of operation to electrosurgical pencil 100.

In operation, if more than one activation switch 410, 420 or 430 is actuated simultaneously (i.e., a "multi-key activation" scenario), electrosurgical generator "G" will measure a unique voltage which does not correspond to any preset known voltage stored therein and thus does not activate or transmit any mode of operation to electrosurgical pencil 100.

One of switches "S2a"-"S2c" may correspond to the hemostatic/coagulation effect/function which can be defined as having waveforms with a duty cycle from about 1% to about 12%. Another of switches "S2a"-"S2c" may correspond to the cutting and/or dissecting effect/function which can be defined as having waveforms with a duty cycle from about 75% to about 100%. The last of switches "S2a"-"S2c" may correspond to a bi-polar sealing function which may automatically perform a sealing function based on sensor feedback and generator "G" control. It is important to note that these percentages are approximated and may be customized to deliver the desired surgical effect for various tissue types and characteristics.

VDN 450 may further include safety switch "S3" and safety switch "S3'" for disabling bipolar or monopolar activation depending on the position of jaw member 330 and 340. Safety switch "S3" is disposed in series with switch "S2c" and may be closed when jaw members 330 and 340 are in the first, open position and open when jaw members 330 and 340 are in the second, closed position. Safety switch "S3'" is disposed in series with each of switches "S2b" and "S2a" and may be closed when jaw members 330 and 340 are in the second, closed position but open when jaw members 330 and 340 are in the first, open position. Safety switch "S3'" may be a single switch disposed in series with a parallel circuit of switches "S2a" and "S2b" or alternatively may be two separate switches "S3'" each disposed in series one of switches "S2a" and "S2b". Safety switch "S3" may also only be closed when tissue is sensed between jaw members 330 and 340 as described below.

Electrosurgical pencil 100 may further include a sensor (not shown) operably coupled to electrosurgical pencil 100 and configured to sense tissue disposed between jaw members 330 and 340. The sensor may provide a signal to controller terminal 460 to disable monopolar activation if tissue is sensed between jaw members 330, 340 by opening safety switch "S3''" or disable bipolar activation if no tissue is sensed between jaw members 330, 340 by opening safety switch "S3". The sensor may also be used to assist in determining the required intensity level and adjustments during bipolar use for sealing or coagulating operations.

As seen throughout FIGS. 1-2, 7 and 36-39, electrosurgical pencil 100 further includes an intensity controller 700 slidingly supported on or in housing 200. Intensity controller 700 includes a pair of nubs 710, 720 which are slidingly supported, one each, in respective guide channels 270, 280, formed in each side shell portion 230, 240 of housing 200, respectively. Guide channels 270, 280 may be formed on either side of activations switches 410, 420, 430. By providing nubs 710, 720 on either side of activation switches 410, 420, 430, intensity controller 700 can be easily manipulated by either hand of the user or the same electrosurgical pencil can be operated by a right-handed or a left-handed user.

As seen in FIGS. 1-2, 7-9 and 36-39, intensity controller 700 further includes an element 730 extending from a bottom surface thereof which contacts and presses into or against VDN 450. In this manner, as intensity controller 700 is displaced in a distal or proximal direction relative to housing 200, element 730 translates relative to VDN 450 to vary the intensity setting being transmitted to jaw members 330, 340, as will be described in greater detail below.

Intensity controller 700 may be configured to function as a slide potentiometer, sliding over and along VDN 450. Intensity controller 700 has a first position wherein nubs 710, 720 are at a proximal-most position (e.g., closest to plug 500 and element 730 being located at a proximal-most position) corresponding to a relative low intensity setting, a second position wherein nubs 710, 720 are at a distal-most position (e.g., closest to jaw members 330, 340 and element 730 being located at a distal-most position) corresponding to a relative high intensity setting, and a plurality of intermediate positions wherein nubs 710, 720 are at positions between the distal-most position and the proximal-most position corresponding to various intermediate intensity settings. As can be appreciated, the intensity settings from the proximal end to the distal end may be reversed, e.g., high to low.

Nubs 710, 720 of intensity controller 700 and corresponding guide channels 270, 280 may be provided with a series of cooperating discreet or detented positions defining a series of positions, e.g., five, to allow easy selection of the output intensity from the low intensity setting to the high intensity setting. The series of cooperating discreet or detented positions also provide the surgeon with a degree of tactile feedback. A plurality of discreet detents 290 may be defined in an inner upper surface of side shell portions 230, 240 for cooperating with and selectively engaging a resilient finger 740 extending upwardly from intensity controller 700. Accordingly, in use, as intensity controller 700 slides distally and proximally, resilient finger 740 selectively engages detents 290 to set the intensity level as well as to provide the user with tactile feedback as to when the intensity controller has been set to the desired intensity setting.

Intensity controller 700 is configured and adapted to adjust the power parameters (e.g., voltage, power and/or current intensity) and/or the power verses impedance curve shape to affect the perceived output intensity during monopolar activation. For example, the greater intensity controller 700 is displaced in a distal direction the greater the level of the power parameters transmitted to jaw members 330, 340. Conceivably, current intensities can range from about 60 mA to about 240 mA when using an electrosurgical blade and having a typical tissue impedance of about 2K ohms. An intensity level of 60 mA provides very light and/or minimal cutting/dissecting/hemostatic effects. An intensity level of 240 mA provides very aggressive cutting/dissecting/hemostatic effects. Accordingly, the preferred range of current intensity is from about 100 mA to about 200 mA at 2K ohms. During bipolar operation, the intensity controller 700 is inoperable.

The intensity settings may be preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

When monopolar use is selected, and depending on the particular electrosurgical function desired, the surgeon depresses one of activation switches 410, 420, 430, in the direction indicated by arrow "Y" (see FIGS. 1-2 and 36-37) thereby urging a corresponding tactile element 412, 422, 432 against VDN 450 and thereby transmitting a respective characteristic signal to electrosurgical generator "G". For example, the surgeon can depress activation switch 410 to perform a cutting and/or dissecting function, activation switch 420 to perform a blending function, or activation switch 430 to perform a hemostatic function. In turn, generator "G" transmits an appropriate waveform output to jaw members 330 and or 340 via RF lines 530 and 532. In monopolar mode, intensity controller 700 is activated to allow the surgeon to make intensity adjustments. As the surgeon manipulates intensity controller 700, electrosurgical energy is provided to one or both jaw members 330, 340 at a single potential. A return pad is applied to the patient for receiving the electrosurgical energy. The surgeon manipulates intensity controller 700 until the desired intensity level is achieved and then applies jaw member 330 and or 340 to tissue to perform the surgical procedure.

When bipolar use is selected, each jaw member 330, 340 is set to a different potential and electrosurgical energy is transmitted through tissue disposed therebetween. Intensity controller 700 is deactivated. The surgeon manipulates actuators 350 and 360 to transition jaw members 330, 340 from the second position to the first position, thereby providing a space for receiving tissue. Once the surgeon places jaw members 330, 340 in the desired position, with tissue between jaw members 330, 340, the surgeon releases actuators 350 and 360, allowing jaw members 330, 340 to transition toward the second position and thereby clamp or compress the tissue under a spring bias and proportionally create an appropriate pressure between jaw members 330 and 340. Jaw members 330, 340 may be configured to compress tissue therebetween under working pressure to coagulate tissue or form a tissue seal (e.g., about 3 kg/cm$^2$ to about 16 kg/cm$^2$). To form a seal, jaw members 330, 340 cooperate to compress tissue within the working pressure range while maintaining a gap between jaw members 106$a$, 106$b$ to within the range of 0.001 inches to 0.006 inches. A variety of stop members or stop member arrangements may be utilized to provide the appropriate gap distance between jaw members 330 and 340, e.g., as in U.S. Pat. No. 7,473,253. After the tissue is clamped at the appropriate working pressure and the sensor determines that there is tissue between jaw members 330 and 340, electrosurgical energy is activated either automatically or through manipulation of one of activation switches 410, 420 or 430 by the surgeon to coagulate or seal the tissue. The surgeon then manipulates actuators 350, 360 once more to release the tissue.

It is contemplated that the features found in the above embodiments may be combined with any other embodiment and are not limited to their particular embodiment.

Although the subject apparatus has been described with respect to particular embodiments, it will be readily apparent, to those having ordinary skill in the art to which it appertains, that changes and modifications may be made thereto without departing from the spirit or scope of the subject apparatus.

The invention claimed is:

1. A surgical instrument, comprising:
    first and second jaw members transitionable between a closed position and an open position, the first and second jaw members adapted to connect to a source of energy and configured to treat tissue in both a first mode, wherein the first and second jaw members are energized to the same potential to treat tissue with monopolar energy, and a second mode, wherein the first and second jaw members are energized to different potentials to treat tissue with bipolar energy;
    a sensor disposed on at least one of the first or second jaw members, the sensor configured to sense whether tissue is disposed between the first and second jaw members, the presence of tissue disposed between the first and second jaw members corresponding to the second mode and sense of tissue disposed between the first and second jaw members corresponding to the first mode; and
    a controller in communication with the sensor, the controller configured to disable monopolar activation of the first and second jaw members when the sensor indicates that the first and second jaw members are in the second mode and to disable bipolar activation of the first and second jaw members when the sensor indicates that the first and second jaw members are in the first mode.

2. The surgical instrument according to claim 1, further including a jaw member actuator operably coupled to the first and second jaw members, the jaw member actuator selectively manipulatable for transitioning the first and second jaw members between the closed and open positions.

3. The surgical instrument according to claim 2, wherein the jaw member actuator is pressure sensitive and adjusts the position of the first and second jaw members relative to one another based on the amount of pressure applied to the jaw member actuator.

4. The surgical instrument according to claim 1, wherein the first and second jaw members are biased in the closed position.

5. The surgical instrument according to claim 3, wherein the jaw member actuator includes a flexible portion.

6. The surgical instrument according to claim 1, further including at least one switch operably coupled to the controller, the at least one switch configured, in the first mode, to activate the first and second jaw members with monopolar energy, and, in the second mode, to activate the first and second jaw members with bipolar energy.

\* \* \* \* \*